(12) United States Patent
Yamamoto et al.

(10) Patent No.: US 11,364,079 B2
(45) Date of Patent: Jun. 21, 2022

(54) SHOCK WAVE GENERATING DEVICE, AND SHOCK WAVE ABLATION SYSTEM

(71) Applicant: SOUND WAVE INNOVATION CO., LTD., Tokyo (JP)

(72) Inventors: Hiroaki Yamamoto, Miyagi (JP); Kazuyoshi Takayama, Miyagi (JP); Hiroaki Shimokawa, Miyagi (JP)

(73) Assignee: SOUND WAVE INNOVATION CO., LTD., Tokyo (JP)

( * ) Notice: Subject to any disclaimer, the term of this patent is extended or adjusted under 35 U.S.C. 154(b) by 0 days.

(21) Appl. No.: 17/043,040

(22) PCT Filed: Mar. 28, 2019

(86) PCT No.: PCT/JP2019/013827
§ 371 (c)(1),
(2) Date: Dec. 17, 2020

(87) PCT Pub. No.: WO2019/189672
PCT Pub. Date: Oct. 3, 2019

(65) Prior Publication Data
US 2021/0100615 A1  Apr. 8, 2021

(30) Foreign Application Priority Data
Mar. 29, 2018 (JP) .............................. JP2018-066022

(51) Int. Cl.
*A61B 18/20* (2006.01)
*A61B 18/26* (2006.01)
(Continued)

(52) U.S. Cl.
CPC .............. *A61B 18/26* (2013.01); *G02B 6/262* (2013.01); *A61B 2018/00577* (2013.01);
(Continued)

(58) Field of Classification Search
CPC ...................................................... A61B 18/26
See application file for complete search history.

(56) References Cited

U.S. PATENT DOCUMENTS

2013/0274726 A1   10/2013   Takayama et al.
2015/0359557 A1*  12/2015   Shimokawa ............ A61B 18/26
                                                    601/2

FOREIGN PATENT DOCUMENTS

JP    S61193653 A   8/1986
JP    200961083 A   3/2009
(Continued)

OTHER PUBLICATIONS

Yamamoto Hiroaki et al., "Behavior change of underwater shock wave generated by Q-switched Ho:YAG laser beam due to the shape of the fiber tip", Proceedings of Symposium on Shock Waves, 2013, 1B2-6, Japan, 5pp.

*Primary Examiner* — Lynsey C Eiseman
(74) *Attorney, Agent, or Firm* — Hauptman Ham, LLP

(57) ABSTRACT

A shock wave generating device includes an optical fiber and a reflective part, and is configured to reflect and converge the shock wave generated inside the reflective part to an outside of the reflective part. The reflective part includes: a reflector having a concave surface having a cut surface-of-revolution shape, and a through hole, which is formed coaxially with a rotating axis of the concave surface, and into which the optical fiber is to be inserted; a sealing body configured to seal an opening portion of the concave surface; and a liquid to be charged between the concave surface and the sealing body. The optical fiber has a distal end arranged at a position on a rear side of a focal point of the concave surface, at which the shock wave reflected by the concave surface is convergeable outside the reflective part.

6 Claims, 11 Drawing Sheets

(51) Int. Cl.
*G02B 6/26* (2006.01)
*A61B 18/00* (2006.01)
*A61B 18/22* (2006.01)

(52) U.S. Cl.
CPC ............... *A61B 2018/2266* (2013.01); *A61B 2018/2272* (2013.01); *A61B 2018/263* (2013.01)

(56) References Cited

FOREIGN PATENT DOCUMENTS

| | | | |
|---|---|---|---|
| JP | 4635233 | B2 | 2/2011 |
| JP | 201285812 | A | 5/2012 |
| JP | 5435739 | B2 | 3/2014 |

\* cited by examiner

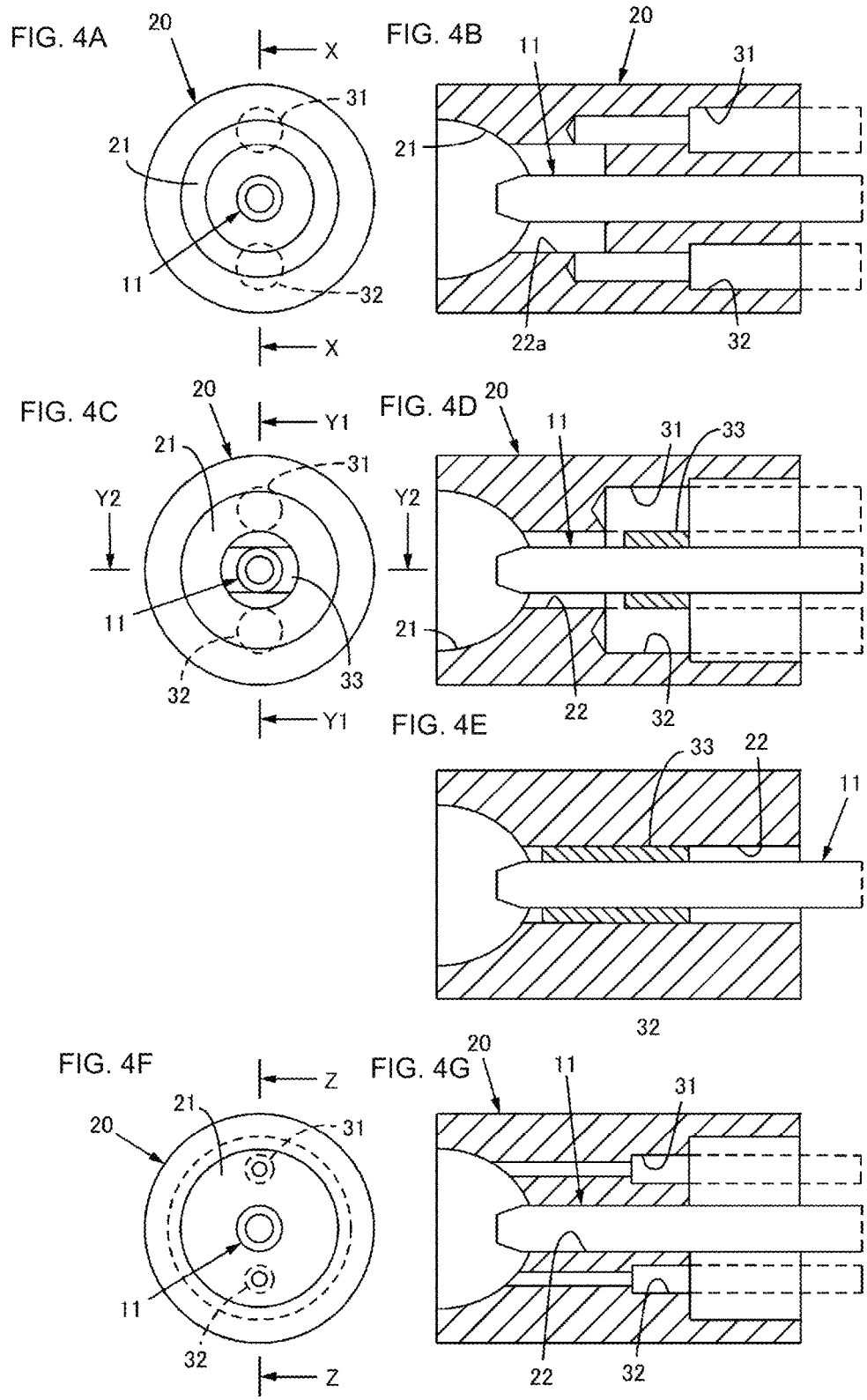

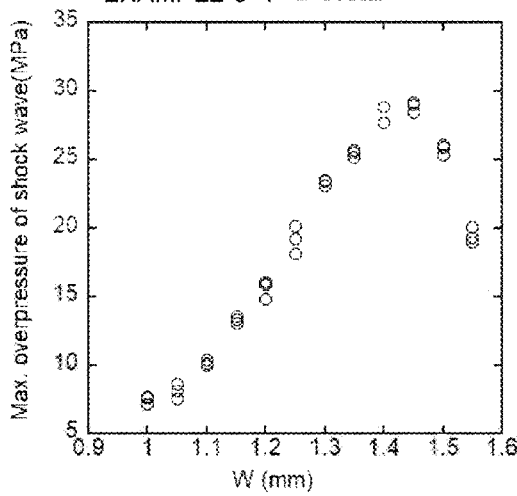
FIG. 11A  EXAMPLE 3-1  M=0.6mm
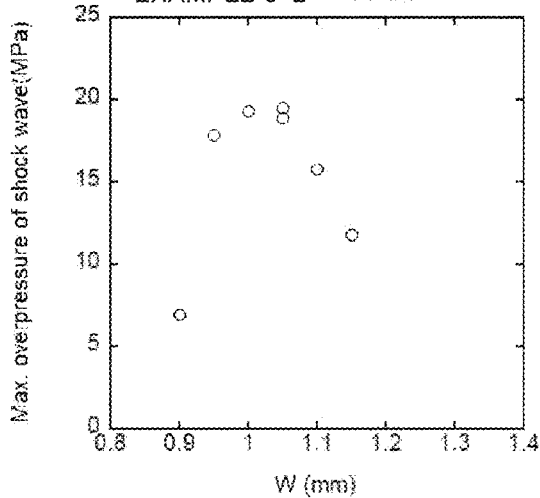
FIG. 11B  EXAMPLE 3-2  M=0.4mm
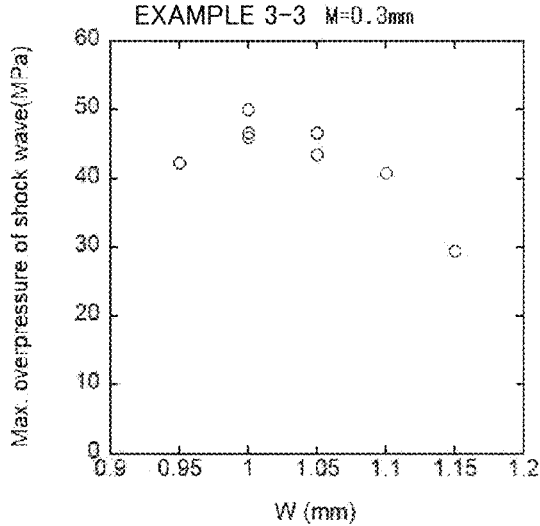
FIG. 11C  EXAMPLE 3-3  M=0.3mm

SHOCK WAVE GENERATING DEVICE, AND SHOCK WAVE ABLATION SYSTEM

RELATED APPLICATIONS

The present application is a National Phase of International Application No. PCT/JP2019/013827 filed Mar. 28, 2019, which claims priority to Japanese Application No. 2018-066022, filed Mar. 29, 2018.

TECHNICAL FIELD

The present invention relates to a shock wave generating device and a shock wave ablation system.

BACKGROUND ART

There is known a shock wave generating device configured to radiate a pulse laser beam underwater, and reflect and converge shock wave generated underwater to crush and remove a stone in a ureter or kidney.

The inventors of the present invention have succeeded in developing, as described in Patent Literature 1, a shock wave generating device including an optical fiber and a cylindrical reflector, the shock wave generating device being downsized to a size that can be incorporated into a catheter. With the shock wave generating device, the inventors have proposed a method of treating arrhythmia, in which a cardiac muscle tissue causing the arrhythmia, in particular, a cardiac muscle tissue in a deep portion is necrotized from an endocardial side through the catheter. The inventors of the present invention have also proposed, as described in Patent Literature 2, an optical fiber suitable for such a shock wave generating device.

Further, the inventors of the present invention have reported, as described in Non-patent Literature 1, that, when a distal end shape of an optical fiber is formed into a truncated cone, a shape of a wave front is different depending on a taper angle α, and the wave front of the shock wave becomes closer to spherical as the taper angle α becomes larger. The inventors have also reported that, when the taper angle α is from 20° to 50°, the wave front of the shock wave swells from a laser emission direction to the rear as the taper angle α becomes smaller, and when the taper angle α is from 30° to 50°, an intensity (overpressure) of the shock wave was maximized.

CITATION LIST

Patent Literature

PTL 1: JP 4635233 B2
PTL 2: JP 5435739 B2

Non-Patent Literature

NPL 1: YAMAMOTO Hiroaki, TAKAYAMA Kazuyoshi, and SHIMOKAWA Hiroaki, "Behavior change of underwater shock wave generated by Q-switched Ho:YAG laser beam due to the shape of the fiber tip," Proceedings of Symposium on Shock Waves in JAPAN 2013, 1B2-6

SUMMARY OF INVENTION

Technical Problem

Meanwhile, in a related-art shock wave generating device, a distal end of an optical fiber is generally arranged to coincide with a focal point of a concave surface of a reflector, and no consideration has been given to the above-mentioned distortion of the wave front of the shock wave. As a result of repeatedly conducting detailed experiments on those points, the inventors of the present invention have found that, through arrangement of the distal end of the optical fiber at a suitable position behind the focal point of the concave surface, the shock wave can be efficiently reflected and converged to one point (convergent point) outside a reflective part, and the overpressure of the shock wave can be increased dramatically.

In other words, the present invention has an object to provide a shock wave generating device and a shock wave ablation system, with which shock wave generated in a liquid can be efficiently reflected and converged.

Solution to Problem

According to one embodiment of the present invention, there is provided a shock wave generating device including: an optical fiber; and a reflective part, the shock wave generating device being configured to reflect and converge shock wave generated inside the reflective part to an outside of the reflective part, the reflective part including: a reflector having a concave surface, which is provided on one end side, and has a cut surface-of-revolution shape obtained by cutting a spheroid in which a major axis is a rotating axis, or a curved surface obtained by modifying the spheroid, and a through hole, which is formed coaxially with the rotating axis, and into which the optical fiber is to be inserted from the other end side; a sealing body configured to seal an opening portion of the concave surface; and a liquid to be charged between the concave surface and the sealing body, the optical fiber having a distal end arranged at a position on the another end side of a focal point of the concave surface in the reflective part, at which the shock wave reflected by the concave surface is convergeable outside the reflective part.

In the present invention, the "concave surface obtained by cutting the spheroid in which the major axis is the rotating axis, or the curved surface obtained by modifying the spheroid" refers to a concave surface obtained by cutting the spheroid, or the curved surface obtained by modifying the spheroid, by a plane other than a plane parallel to the rotating axis.

According to the shock wave generating device of the present invention, the distal end of the optical fiber is arranged at a position on the another end side of the focal point of the concave surface in the reflective part, at which the shock wave reflected by the concave surface is convergeable outside the reflective part. Therefore, when a pulse laser beam is radiated from the distal end of the optical fiber to generate the shock wave in the liquid, the generation center of the shock wave and the focal point of the concave surface can substantially coincide with each other, and as a result, the shock wave reflected by the concave surface can be efficiently converged to one point outside the reflective part.

In the shock wave generating device according to one embodiment of the present invention, it is preferred that the optical fiber include, in a distal end portion thereof, a laser beam convergence part having a truncated cone shape. In this case, the pulse laser beam can be focused in front of the laser beam convergence part, and large shock wave can be generated in the liquid.

In the shock wave generating device according to one embodiment of the present invention, it is preferred that a distance Lx from a distal end of the laser beam convergence part to the focal point satisfy [Equation 1] and [Equation 2]:

$$0 < \frac{Lx}{d} \leq 1.5 \quad \text{[Equation 1]}$$

(I) When $\frac{n_{qtz}}{n_{liq}} \sin\left(0.5\alpha + \cos^{-1}\left(\frac{NA}{n_{qtz}}\right)\right) > 1,$ [Equation 2]

$$d = \frac{0.5M - h \tan 0.5\alpha}{\tan\left(\sin^{-1}\frac{n_{qtz}}{n_{liq}}\sin\left(\alpha + \sin^{-1}\frac{NA}{n_{qtz}}\right)\right)}$$

(II) When $\frac{n_{qtz}}{n_{liq}} \sin\left(-0.5\alpha + \cos^{-1}\left(\frac{NA}{n_{qtz}}\right)\right) \leq 1,$ $$\frac{n_{qtz}}{n_{liq}} \sin(0.5\pi - 0.5\alpha) > 1,$$

$$d = \frac{0.5M - h \tan 0.5\alpha}{\tan\left(\sin^{-1}\frac{n_{qtz}}{n_{liq}}\sin\left(\alpha - \sin^{-1}\frac{NA}{n_{qtz}}\right)\right)}$$

provided that, in [Equation 2], "α" represents an angle formed by an isosceles trapezoid expressed by a cross section in an axial direction of the laser beam convergence part, "$n_{qtz}$" represents a refractive index of a core of the optical fiber, "$n_{liq}$" represents a refractive index of the liquid, "NA" represents a numerical aperture of the optical fiber, "M" represents a core diameter in a proximal end portion of the laser beam convergence part, and "h" represents a height of a truncated cone of the laser beam convergence part.

Condition (I) in "Equation 2" is a condition in which substantially all the pulse laser beam is totally reflected, and Condition (II) is a condition in which a part of the pulse laser beam is totally reflected, and the other part thereof is transmitted.

Further, "d" in each of Conditions (I) and (II) of "Equation 2" represents, when the pulse laser beam totally reflected in the laser beam convergence part is radiated from the distal end of the laser beam convergence part and is focused in front of the laser beam convergence part, a theoretical value of a distance between a focusing point of the pulse laser beam and the distal end of the laser beam convergence part.

In the shock wave generating device according to one embodiment of the present invention, it is preferred that a distance Lx from a distal end of the laser beam convergence part to the focal point satisfy [Equation 3] and [Equation 4]:

$$0 < \frac{Lx}{d} \leq 2 \quad \text{[Equation 3]}$$

(III) When $\frac{n_{qtz}}{n_{liq}} \sin(0.5\pi - 0.5\alpha) \leq 1,$ [Equation 4]

$$\frac{n_{qtz}}{n_{liq}} \sin\left(-0.5\alpha + 0.5\pi + \sin^{-1}\left(\frac{NA}{n_{qtz}}\right)\right) > 1,$$

$$d = (0.5M - h \tan(0.5\alpha)) \tan\left(\pi - 0.5\alpha - \sin^{-1}\left(\frac{n_{qtz}}{n_{liq}}\cos(0.5\alpha)\right)\right)$$

provided that, in [Equation 4], "α" represents an angle formed by an isosceles trapezoid expressed by a cross section in an axial direction of the laser beam convergence part, "$n_{qtz}$" represents a refractive index of a core of the optical fiber, "$n_{liq}$" represents a refractive index of the liquid, "NA" represents a numerical aperture of the optical fiber, "M" represents a core diameter in a proximal end portion of the laser beam convergence part, and "h" represents a height of a truncated cone of the laser beam convergence part.

Condition (III) in "Equation 4" is a condition in which a part of the pulse laser beam other than a particular part thereof is transmitted through the laser beam convergence part.

Further, in "Equation 4," "d" represents, when the part of the pulse laser beam that has transmitted through the laser beam convergence part is focused in front of the laser beam convergence part, a theoretical value of a distance between a focusing point of the pulse laser beam and the distal end of the laser beam convergence part.

In the shock wave generating device according to one embodiment of the present invention, it is preferred that the concave surface be a cut surface of revolution obtained by cutting a curved surface obtained by rotating a shape $(x_1, y_1)$ determined by [Equation 5] and [Equation 6] with a major axis of an ellipse expressed by [Equation 5] being a rotating axis, $$\frac{x^2}{a^2} + \frac{y^2}{b^2} = 1, 1.2 < \frac{a}{b} < 2.0, b \leq 50 \quad \text{[Equation 5]}$$

$$x_1 = x + 0.5\Delta D |\cos \theta|, y_1 = y + 0.5\Delta D \sin \theta, 0 \leq \theta \leq \pi \quad \text{[Equation 6]}$$

provided that, in [Equation 6], "θ" represents, when a wave front of the shock wave at a certain time is represented by S, a wave front of ideal shock wave assuming shock wave to be completely spherical is represented by I, a center point of the ideal shock wave is represented by C, and a point on the wave front S and the wave front I that is located on an extension of a center axis of the optical fiber is represented by $S_f$, an angle around the center point C with respect to a line connecting the center point C and the point $S_f$, and "ΔD" represents, when points of intersection of a straight line in a radial direction of the ideal shock wave that passes through the center point C and has a central angle of θ, and the wave front S and the wave front I are represented by $S_θ$ and $I_θ$, respectively, a distance between the point of intersection Se and the point of intersection $I_θ$.

Through the modification of the concave surface as described above, propagation distances over which the shock wave generated at a focal point of the spheroid before the modification is reflected at different portions of the concave surface and is converged to one point outside the reflective part can be equalized. Therefore, even when the shock wave is aspherical, the shock wave can be efficiently reflected and converged.

According to one embodiment of the present invention, there is provided a shock wave ablation system including: the shock wave generating device of one embodiment of the present invention; and a catheter having the shock wave generating device fixed to a distal end thereof. Therefore, the overpressure of the shock wave is high, and can be suitably used for ablation treatment for arrhythmia, for example.

BRIEF DESCRIPTION OF DRAWINGS

FIG. 4A is a front view for illustrating an embodiment in which a plumbing structure for perfusing a space formed between a concave surface and a sealing body with a liquid to be charged is provided, FIG. 4B is a cross-sectional view taken along the line X-X of FIG. 4A, FIG. 4C is a front view for illustrating another embodiment in which a plumbing structure is provided, FIG. 4D and FIG. 4E are cross-sectional views taken along the lines Y1-Y1 and Y2-Y2 of FIG. 4C, respectively, FIG. 4F is a front view for illustrating still another example in which a plumbing structure is provided, and FIG. 4G is a cross-sectional view taken along the line Z-Z of FIG. 4F.

FIG. 11A, FIG. 11B, and FIG. 11C are graphs for showing a relationship between a distance W from an opening portion of the concave surface to the distal end of the optical fiber and the maximum overpressure $P_{max}$ of the shock wave when the core diameter of the optical fiber is 600 μm, when the core diameter of the optical fiber is 400 μm, and when the core diameter of the optical fiber is 300 μm, respectively.

DESCRIPTION OF EMBODIMENTS

1. First Embodiment

First, a shock wave generating device 10 according to a first embodiment of the present invention is described.

Figure 1:
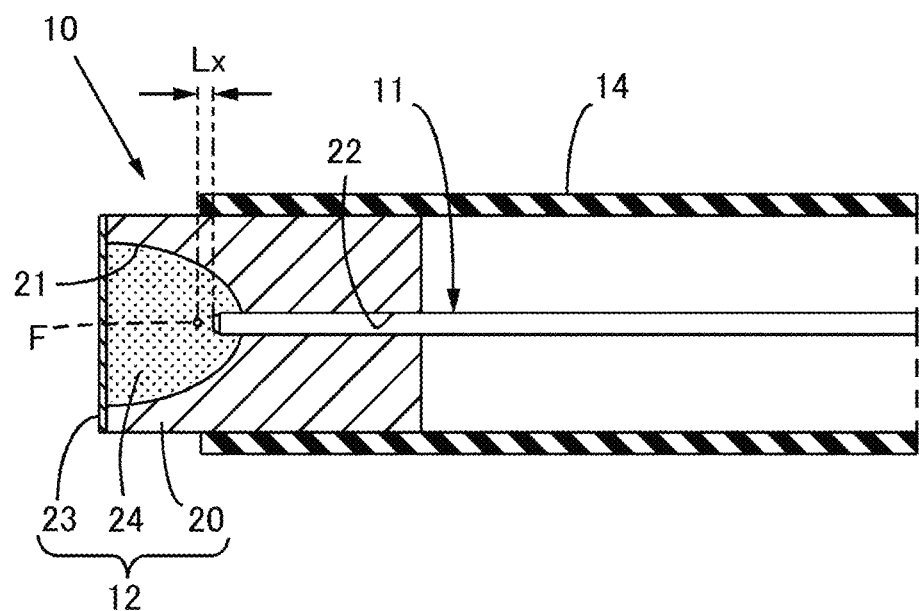
FIG. 1 is a cross-sectional view in an axial direction for illustrating an example of a shock wave generating device according to an embodiment of the present invention.

The shock wave generating device 10 of FIG. 1 includes an optical fiber 11 and a reflective part 12. An emission direction (left side in FIG. 1) of a pulse laser beam in the shock wave generating device 10 of FIG. 1 is defined as the "front," and an opposite direction (right side in FIG. 1) from the emission direction is defined as the "rear."

The reflective part 12 includes: a reflector 20 having a concave surface 21, which is provided on one end side (front side), and is obtained by cutting a spheroid in which a major axis is a rotating axis, or a curved surface obtained by modifying the spheroid, and a through hole 22, which is formed coaxially with the rotating axis of the concave surface 21, and into which the optical fiber 11 is to be inserted from the other end side (rear side); a sealing body 23 configured to seal an opening portion of the concave surface 21; and a liquid 24 to be charged between the concave surface 21 and the sealing body 23.

The optical fiber 11 is inserted into the through hole 22, and hence has a center axis that coincides with the rotating axis of the concave surface 21. Further, the optical fiber 11 has a distal end (end portion on the front side) arranged in the reflective part 12, specifically, in a space formed by the concave surface 21 and the sealing body 23, and on the rear side (right side in FIG. 1) of a focal point F of the concave surface 21.

The shock wave generating device 10 is configured to irradiate the liquid 24 charged between the concave surface 21 and the sealing body 23 with the pulse laser beam through the optical fiber 11 to generate shock wave in the liquid, and reflect the shock wave with the concave surface 21 to converge the shock wave to one point outside the reflective part 12. As a result, even when an affected area is in a deep layer of a cardiac muscle tissue, for example, an affected tissue can be necrotized.

The shock wave generating device has a relatively simple structure, and hence can be downsized and easily attached to a distal end of a catheter 14. In this case, the shock wave generating device can be used as a shock wave ablation system, which is applicable to ablation treatment for arrhythmia, for example.

Figure 2A:
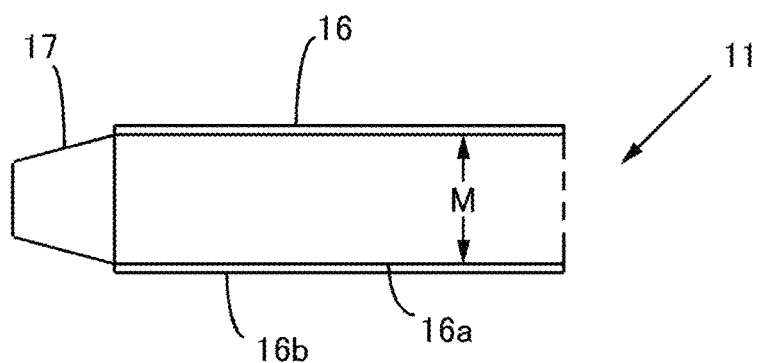
FIG. 2A is a cross-sectional view in the axial direction for illustrating an optical fiber.

It is preferred that the optical fiber 11 be formed, as illustrated in FIG. 2A, of a linear main body part 16 and a laser beam convergence part 17, which is provided in a distal end portion (end portion on an emission side of the pulse laser beam). The main body part 16 includes a core 16a and a clad 16b, which is provided around the perimeter of the core 16a. Further, the main body part 16 has flexibility. The perimeter of the clad 16b may be sheathed.

The core 16a of the optical fiber 11 is not particularly limited, and a core made of a resin or glass may be used. However, it is preferred that the core be made of quartz, in particular, dehydroxylated quartz. A refractive index $n_{qtz}$ of the core 16a is preferably from 1.3 to 1.8, and more preferably from 1.4 to 1.6. Further, a diameter (hereinafter referred to as "core diameter") M of the core 16a is preferably from 10 μm to 2,000 μm, more preferably from 50 μm to 1,000 μm, and particularly preferably from 100 μm to 600 μm.

Meanwhile, the clad 16b is not particularly limited as long as the clad 16b has a refractive index that is lower than the refractive index $n_{qtz}$ of the core 16a, and a clad made of a resin or glass may be used. However, it is preferred that the clad be made of quartz. The refractive index of the clad 16b is preferably from 1.0 to 1.5, and more preferably from 1.3 to 1.4. A numerical aperture NA of the main body of the optical fiber 11 is preferably from 0 to 0.9, and is more preferably from 0 to 0.3.

Figure 2B:
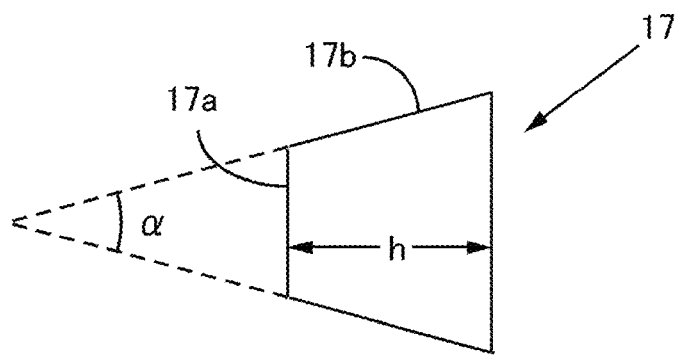
FIG. 2B is a partially enlarged view of FIG. 2A.

It is preferred that the laser beam convergence part 17 be formed so that a diameter thereof becomes smaller toward a distal end. For example, as with the optical fiber described in Patent Literature 2, the distal end may be formed so that, in a cross section along the axial direction (hereinafter referred to as "cross section in the axial direction") that is a plane perpendicular to an axial direction, an interior angle with respect to a deformation direction of sides may become gradually smaller toward the distal end. However, it is more preferred that, as illustrated in FIG. 2B, the laser beam convergence part 17 be formed into a truncated cone shape having a diameter that becomes smaller toward the distal end. In this case, the laser beam convergence part 17 and the main body part 16 are coaxial with each other. With the shape expressed by the cross section in the axial direction of the laser beam convergence part 17 being substantially an isosceles trapezoid as described above, that is, with both sides 17b of the trapezoid being inclined at substantially the same angle and a distal end surface 17a (short base) being flat, the pulse laser beam can be efficiently focused in front of the laser beam convergence part 17. Specifically, the pulse laser beam totally reflected by an interior surface of the sides 17b of the laser beam convergence part 17 is focused inside the laser beam convergence part 17, and is radiated from the distal end surface 17a of the laser beam convergence part. Then, the pulse laser beam radiated from the distal end surface 17a of the laser beam convergence part is focused in front of the laser beam convergence part 17 (see FIG. 3A and FIG. 3B). Meanwhile, the pulse laser beam transmitted through the laser beam convergence part 17 is transmitted through the sides 17b of the laser beam convergence part 17, and is focused in front of the laser beam convergence part 17 (see FIG. 3C). In this manner, irrespective of whether the pulse laser beam is totally reflected by, or transmitted through, the laser beam convergence part 17, the laser beam convergence part 17 can converge the pulse laser beam in front of the laser beam convergence part 17.

It is preferred that a surface of the core of the laser beam convergence part 17 be a mirror surface and be devoid of fine cracks or asperities. With the surface of the core of the laser beam convergence part 17 being a mirror surface as described above, absorption of the pulse laser beam at an interface can be avoided. Further, it is possible to prevent water from penetrating the fine cracks or asperities in the surface of the core of the laser beam convergence part 17 and destructing the laser beam convergence part 17 with the cracks as the origins. A "mirror surface" as used herein refers to a state in which an arithmetic average roughness Ra is 0.05 μm or less, and preferably 0.01 μm or less. Such a mirror surface can be formed by known methods, such as mechanical polishing, laser polishing, cleaving, and annealing. For example, when a mirror surface is to be formed by mechanical polishing, the mirror surface can be formed through polishing with the use of a plurality of abrasives having different average particle sizes.

More specifically, the mirror surface can be formed through polishing with the use of the abrasives in order of decreasing average particle size, and finally with the use of an abrasive having an average particle size of 10 μm or less, preferably 5 μm or less, and more preferably 1 μm or less. Annealing is further performed to eliminate fine cracks or asperities formed during polishing.

An angle (taper angle) α formed by the both sides 17b of the isosceles trapezoid in the cross section in the axial direction of the laser beam convergence part 17 is from 5° to 80°, preferably from 10° to 70°, and particularly preferably from 15° to 65°.

With the angle α being from 5° to 80° as described above, the pulse laser beam can be efficiently converged to generate larger shock wave. When the angle α is smaller than 5°, the pulse laser beam cannot be converged enough to obtain large shock wave. In contrast, when the angle α is larger than 80°, the pulse laser beam is disadvantageously converged inside the laser beam convergence part 17, and large shock wave cannot be obtained either. Further, the generation center of the shock wave becomes closer to the distal end of the laser beam convergence part 17 of the optical fiber, and the optical fiber is prone to damage.

Meanwhile, it is preferred that a height "h" of the isosceles trapezoid in the cross section in the axial direction of the laser beam convergence part 17 satisfy [Equation 7].

$$h \leq M \bigg/ \left(2 \tan\left(\alpha + \sin^{-1}\frac{NA}{n_{qtz}}\right)\right) \quad \text{[Equation 7]}$$

In [Equation 7], "M" represents a core diameter of a proximal end portion (main body of the optical fiber) of the laser beam convergence part, "NA" represents a numerical aperture of the main body of the optical fiber, and "$n_{qtz}$" represents a refractive index of the core of the optical fiber.

When the height "h" does not satisfy [Equation 7], the pulse laser beam is converged inside the optical fiber 11, and there is a risk of destructing the optical fiber 11. For example, when the core diameter M of the optical fiber to be used is 400 μm, α is 30°, the numerical aperture NA is 0.22, and the refractive index $n_{qtz}$ of the core is 1.437, the upper limit of the height "h" is 0.3 mm or less, preferably 0.28 mm or less, and particularly preferably 0.25 mm or less.

In contrast, when the height "h" is too small, the pulse laser beam cannot be focused enough to obtain large shock wave. A lower limit of the height "h" is different depending on a condition of the optical fiber, but is generally 0.01 mm or more, preferably 0.05 mm or more, and particularly preferably 0.15 mm or more.

Returning to FIG. 1, in the shock wave generating device 10 according to the present invention, the optical fiber 11 has the distal end (end portion on the pulse laser beam emission side) arranged on the rear side (right side in FIG. 1) of the focal point F of the concave surface 21 in the reflective part 12. It is particularly preferred that the distal end be arranged so that a distance Lx between the distal end of the laser beam convergence part 17 and the focal point F satisfy the following [Equation 1] and [Equation 2]:

$$0 < \frac{Lx}{d} \leq 1.5 \quad \text{[Equation 1]}$$

(I) When $\frac{n_{qtz}}{n_{liq}} \sin\left(-0.5\alpha + \cos^{-1}\left(\frac{NA}{n_{qtz}}\right)\right) > 1$, [Equation 2]

$$d = \frac{0.5M - h \tan 0.5\alpha}{\tan\left(\sin^{-1}\frac{n_{qtz}}{n_{liq}}\sin\left(\alpha + \sin^{-1}\frac{NA}{n_{qtz}}\right)\right)}$$

(II) When $\frac{n_{qtz}}{n_{liq}} \sin\left(-0.5\alpha + \cos^{-1}\left(\frac{NA}{n_{qtz}}\right)\right) \leq 1$, $$\frac{n_{qtz}}{n_{liq}} \sin(0.5\pi - 0.5\alpha) > 1,$$

$$d = \frac{0.5M - h \tan 0.5\alpha}{\tan\left(\sin^{-1}\frac{n_{qtz}}{n_{liq}}\sin\left(\alpha - \sin^{-1}\frac{NA}{n_{qtz}}\right)\right)}$$

provided that, in [Equation 2], "α" represents an angle formed by the isosceles trapezoid expressed by the cross section in the axial direction of the laser beam convergence part, "$n_{qtz}$" represents a refractive index of the core of the optical fiber, "$n_{liq}$" represents a refractive index of the liquid, "NA" represents a numerical aperture of the optical fiber, "M" represents a core diameter in the proximal end portion of the laser beam convergence part, and "h" represents a height of the truncated cone of the laser beam convergence part.

Here, Condition (I) in "Equation 2" is a condition in which all the pulse laser beam is totally reflected by the sides (inclined surface) 17b of the laser beam convergence part 17.

Figure 3A:
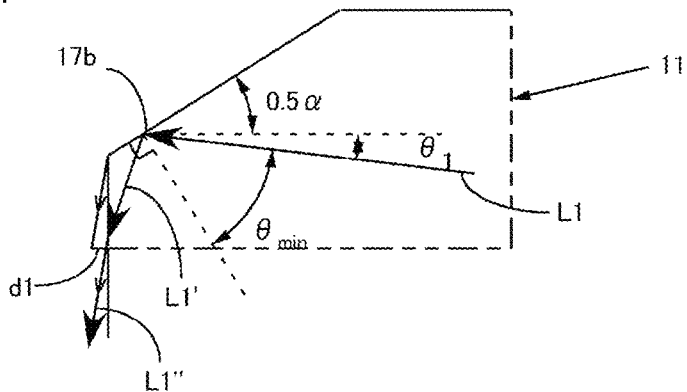
FIG. 3A, FIG. 3B, FIG. 3C, and FIG. 3D are each a schematic diagram for illustrating a pulse laser beam at a predetermined incident angle traveling in the optical fiber.

Specifically, as illustrated in FIG. 3A, a pulse laser beam L1 that travels inside the optical fiber 11 having the numerical aperture NA with a critical angle $\theta_1$, and that enters the sides 17b of the laser beam convergence part 17 at an incident angle $\theta_{min}$ ($0.5\pi-(0.5\alpha+\theta 1)$) is totally reflected. This condition is expressed as:

$$\theta_1 = \sin^{-1}\left(\frac{NA}{n_{qtz}}\right), \frac{n_{qtz}}{n_{liq}}\sin(0.5\pi - (0.5\alpha + \theta_1)) > 1, \qquad [\text{Equation 8}]$$

which results in that:

$$\frac{n_{qtz}}{n_{liq}}\sin\left(-0.5\alpha + \cos^{-1}\left(\frac{NA}{n_{qtz}}\right)\right) > 1. \qquad [\text{Equation 9}]$$

Further, the following [Equation 10] expresses a theoretical value of a distance "d" (d1 in FIG. 3A) between a focusing point obtained when, under the condition, the totally reflected pulse laser beam L1' is radiated from the distal end of the laser beam convergence part 17, and the radiated pulse laser L1" is focused in front of the laser beam convergence part 17, and the distal end of the laser beam convergence part 17.

$$d = \frac{0.5M - h\tan 0.5\alpha}{\tan\left(\sin^{-1}\frac{n_{qtz}}{n_{liq}}\sin\left(\alpha + \sin^{-1}\frac{NA}{n_{qtz}}\right)\right)} \qquad [\text{Equation 10}]$$

Under Condition (I), all the pulse laser beam is totally reflected inside the laser beam convergence part 17, and hence energy loss is the smallest as compared to Conditions (II) and (III).

Condition (II) in "Equation 2" is a condition in which a part of the pulse laser beam is totally reflected by the sides (inclined surface) 17b of the laser beam convergence part 17, and the other part thereof is transmitted.

Specifically, as illustrated in FIG. 3A, a pulse laser beam L1 that travels inside the optical fiber 11 having the numerical aperture NA with the critical angle $\theta_1$, and that enters the sides 17b of the laser beam convergence part 17 at an incident angle $\theta_{min}$ ($0.5\pi-(0.5\alpha+\theta_1)$) is transmitted. This condition is expressed as:

$$\theta_1 = \sin^{-1}\left(\frac{NA}{n_{qtz}}\right), \frac{n_{qtz}}{n_{liq}}\sin(0.5\pi - (0.5\alpha + \theta_1)) \leq 1, \qquad [\text{Equation 11}]$$

which results in that:

$$\frac{n_{qtz}}{n_{liq}}\sin\left(-0.5\alpha + \cos^{-1}\left(\frac{NA}{n_{qtz}}\right)\right) \leq 1. \qquad [\text{Equation 12}]$$

Figure 3B:
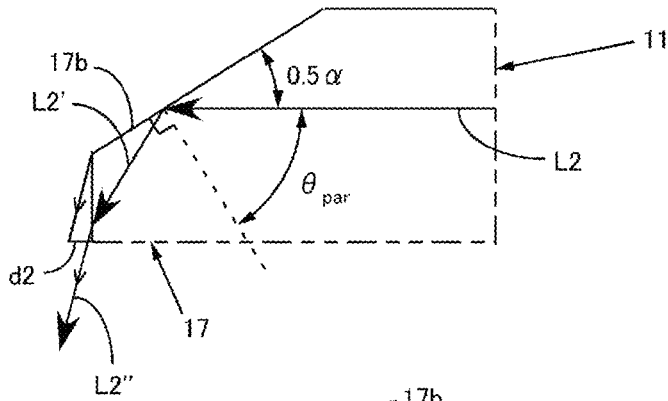

Further, as illustrated in FIG. 3B, a pulse laser beam L2 (incident angle $\theta_{par}$) that travels inside the optical fiber 11 in parallel to the axis thereof is totally reflected. This condition is expressed as:

$$\frac{n_{qtz}}{n_{liq}}\sin(0.5\pi - 0.5\alpha) > 1. \qquad [\text{Equation 13}]$$

In other words, the pulse laser beam entering the sides 17b of the laser beam convergence part 17 at an incident angle that is larger than an angle $\theta_{min}$ ($0.5\pi-(0.5\alpha+\theta_1)$) and is smaller than an angle $\theta_{par}$ ($0.5\pi-0.5\alpha$) is transmitted through the sides 17b of the laser beam convergence part 17, and the pulse laser beam that enters the sides 17b at an incident angle that is the angle $\theta_{par}$ ($0.5\pi-0.5\alpha$) or more is totally reflected by the sides 17b of the laser beam convergence part 17.

Further, the following [Equation 14] expresses a theoretical value of a distance "d" (d2 in FIG. 3B) between a focusing point obtained when, under the condition, the totally reflected part of the pulse laser beam L2' is radiated from the distal end of the laser beam convergence part 17, and the radiated pulse laser beam L2" is focused in front of the laser beam convergence part 17, and the distal end of the laser beam convergence part 17.

$$d = \frac{0.5M - h\tan 0.5\alpha}{\tan\left(\sin^{-1}\frac{n_{qtz}}{n_{liq}}\sin\left(\alpha - \sin^{-1}\frac{NA}{n_{qtz}}\right)\right)} \qquad [\text{Equation 14}]$$

It has been experimentally confirmed that, under Condition (II), as the taper angle $\alpha$ of the laser beam convergence part 17 is increased, the total reflection of the pulse laser beam on the sides 17b of the laser beam convergence part 17 is abruptly reduced, and the effect of the pulse laser beam transmitted through the laser beam convergence part 17 becomes more significant. Therefore, in Condition (II), it is preferred that the taper angle $\alpha$ of the laser beam convergence part 17 be 50° or less, preferably 45° or less, and particularly preferably 40° or less.

From the above-mentioned relationships, it is considered that, when the distance Lx between the laser beam convergence part 17 and the focal point F matches the theoretical value "d" in Conditions (I) and (II) of "Equation 2," that is, when the relationship: Lx=d is established, the shock wave reflected by the concave surface 21 can be converged to one point outside the reflective part 12, and a maximum overpressure $P_{max}$ of the shock wave can be maximized. It should be noted, however, that in an actual shock wave generating device 10, due to the effects such as a type of the pulse laser beam to be used, characteristics of the sealing body 23, and an absorptance of the liquid 24, the maximum overpressure $P_{max}$ is not necessarily maximized when the relationship: Lx=d is established. Further, in Condition (II) of "Equation 2," there are also the effects of the part of the pulse laser beam transmitted through the laser beam convergence part 17. Therefore, it is preferred that the position of the distal end of the laser beam convergence part 17 be appropriately adjusted around the position at which Lx=d. The inventors of the present invention have experimentally confirmed that, in Condition (I), in a range in which the distance Lx is larger than 0 times the theoretical value "d", is preferably 0.4 times the theoretical value "d" or more, and is more preferably 0.5 times the theoretical value "d" or more, and the distance Lx is 1.5 times the theoretical value "d" or less, preferably 1.4 times the theoretical value "d" or less, and more preferably 1.2 times the theoretical value "d" or less, the maximum value of the maximum overpressure $P_{max}$ is obtained. The inventors of the present invention have also experimentally confirmed that, in Condition (II), in a range in which the distance Lx is larger than 0 times the theoretical value "d", is preferably 0.4 times the theoretical value "d" or more, and is more preferably 0.5 times the theoretical value "d" or more, and the distance Lx is 1.5 times the theoretical value "d" or less, preferably 1.3 times the theoretical value "d" or less, and more preferably 1.2 times the theoretical value "d" or less, the maximum value of the maximum overpressure $P_{max}$ is obtained.

Conditions (I) and (II) in "Equation 2" are conditions in which the pulse laser beam totally reflected in the laser beam convergence part 17 is focused. Meanwhile, the inventors of the present invention have experimentally confirmed that the pulse laser beam transmitted through the laser beam convergence part 17 is also focused in front of the laser beam convergence part 17. Therefore, the distal end may be arranged so that the distance Lx between the distal end of the laser beam convergence part 17 and the focal point F satisfies the following [Equation 3] and [Equation 4]:

$$0 < \frac{L_x}{d} \leq 2 \quad \text{[Equation 3]}$$

(III) When $\frac{n_{qtz}}{n_{liq}} \sin(0.5\pi - 0.5\alpha) \leq 1$, [Equation 4]

$$\frac{n_{qtz}}{n_{liq}} \sin\left(-0.5\alpha + 0.5\pi + \sin^{-1}\left(\frac{NA}{n_{qtz}}\right)\right) > 1,$$

$$d = (0.5M - h\tan(0.5\alpha)) \tan\left(\pi - 0.5\alpha - \sin^{-1}\left(\frac{n_{qtz}}{n_{liq}} \cos(0.5\alpha)\right)\right)$$

provided that, in [Equation 4], "α" represents an angle formed by the isosceles trapezoid expressed by the cross section in the axial direction of the laser beam convergence part, "$n_{qtz}$" represents a refractive index of the core of the optical fiber, "$n_{liq}$" represents a refractive index of the liquid, "NA" represents a numerical aperture of the optical fiber, "M" represents a core diameter in a proximal end portion of the laser beam convergence part, and "h" represents a height of the truncated cone of the laser beam convergence part.

Condition (III) in "Equation 4" is a condition in which substantially all the pulse laser beam is transmitted through the sides 17b of the laser beam convergence part 17.

Figure 3C:
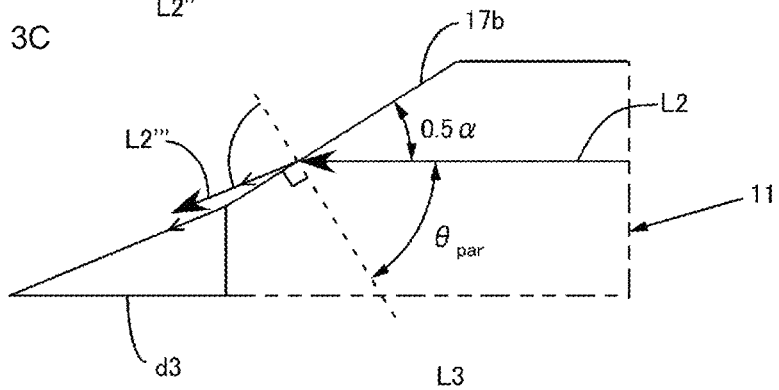

Specifically, as illustrated in FIG. 3C, the pulse laser beam L2 (incident angle $\theta_{par}$) that travels inside the optical fiber 11 in parallel to the axis thereof is transmitted. This condition is expressed as:

$$\frac{n_{qtz}}{n_{liq}} \sin(0.5\pi - 0.5\alpha) \leq 1. \quad \text{[Equation 15]}$$

Figure 3D:
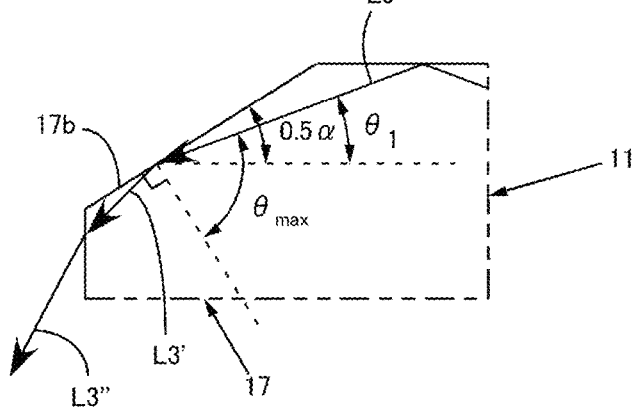

Further, as illustrated in FIG. 3D, a pulse laser beam L3 that travels inside the optical fiber 11 having the numerical aperture NA with the critical angle $\theta_1$, and that enters the sides 17b of the laser beam convergence part 17 at an incident angle $\theta_{max}(0.5\pi-(0.5\alpha-\theta_1))$ is totally reflected. This condition is expressed as follows.

$$\theta_1 = \sin^{-1}\left(\frac{NA}{n_{qtz}}\right), \frac{n_{qtz}}{n_{liq}} \sin(0.5\pi - (0.5\alpha - \theta_1)) > 1 \quad \text{[Equation 16]}$$

That is, only the pulse laser beam that enters the sides 17b of the laser beam convergence part 17 at an incident angle of an angle $\theta_{max}$ ($0.5\pi-(0.5\alpha-\theta_1)$) is totally reflected by the sides 17b of the laser beam convergence part 17, and other beams are transmitted.

Further, the following [Equation 15] expresses a theoretical value of a distance "d" (d3 in FIG. 3C) between a focusing point obtained when, under the condition, the pulse laser beam L2''' transmitted through the sides 17b of the laser beam convergence part 17 is focused, and the distal end of the laser beam convergence part 17.

$$d = (0.5M - h\tan(0.5\alpha)) \quad \text{[Equation 17]}$$
$$\tan\left(\pi - 0.5\alpha - \sin^{-1}\left(\frac{n_{qtz}}{n_{liq}} \cos(0.5\alpha)\right)\right)$$

Also under Condition (III) of "Equation 4," it is considered that, when the distance Lx between the laser beam convergence part 17 and the focal point F matches the theoretical value "d," that is, when the relationship: Lx=d is established, the shock wave reflected by the concave surface 21 can be converged to one point outside the reflective part 12, and the maximum overpressure $P_{max}$ of the shock wave can be maximized. It should be noted, however, that also in this case, in an actual shock wave generating device 10, due to the effects such as the type of the pulse laser beam to be used, the characteristics of the sealing body 23, and the absorptance of the liquid 24, the maximum overpressure $P_{max}$ is not necessarily maximized when the relationship: Lx=d is established. Further, in Condition (III) of "Equation 4," there are also the effects of the particular pulse laser beam totally reflected by the laser beam convergence part 17. Therefore, it is preferred that the position of the distal end of the laser beam convergence part 17 be appropriately adjusted around the position at which Lx=d. The inventors of the present invention have experimentally confirmed that, in the case of Condition (III), in a range in which the distance Lx is larger than 0 as the theoretical value "d," is preferably 0.5 times the theoretical value "d" or more, and is more preferably 0.7 times the theoretical value "d" or more, and the distance Lx is 2.4 times the theoretical value "d" or less, preferably 1.75 times the theoretical value "d" or less, and more preferably 1.6 times the theoretical value "d" or less, the maximum value of the maximum overpressure $P_{max}$ is obtained.

As described above, the shock wave generating device 10 according to the present invention is configured to irradiate the liquid with the pulse laser beam through the optical fiber so that a center point C of the shock wave generated in the liquid coincides with the focal point F of the concave surface 21, or is located extremely close to the focal point F of the concave surface 21. Therefore, the shock wave reflected by the concave surface 21 can be efficiently converged to one point outside the reflective part 12, and the maximum overpressure $P_{max}$ of the shock wave can be increased dramatically.

Next, the reflective part 12 is described. The reflective part 12 has a cylindrical appearance, and includes the reflector 20, the sealing body 23, and the liquid 24. The reflector 20 has the concave surface 21 formed on the front side. The opening portion of the concave surface 21 is sealed by the sealing body 23 with the liquid 24 being charged. Further, the reflector 20 has the through hole 22 formed coaxially with a center axis of the reflector 20 from the rear side toward the concave surface 21. In this manner, the reflective part 12 has a simple structure and can be downsized, and hence can be easily attached to the distal end of the catheter 14.

The concave surface 21 has a cut surface-of-revolution shape obtained by cutting a surface of revolution with a plane perpendicular to the rotating axis or a plane having an inclination angle, for example, so that a propagation direction side (front side) of the shock wave is opened. The concave surface 21 is preferably a cut surface of revolution obtained by cutting the surface of revolution with the plane perpendicular to the rotating axis. The rotating axis of the concave surface 21 is coaxial with the through hole 22.

As the surface of revolution, an ellipsoidal shape satisfying [Equation 5] in which a major axis is the rotating axis is exemplified.

$$\frac{x^2}{a^2} + \frac{y^2}{b^2} = 1, 1.2 < \frac{a}{b} < 2.0, b \leq 50 \quad \text{[Equation 5]}$$

When the concave surface 21 has a cut spheroidal shape, the distal end of the laser beam convergence part 17 of the optical fiber 11 is arranged, in coordinates of [Equation 5], at the following position:

$$(\sqrt{a^2 b^2} + L_x, 0)$$

The ellipsoidal shape expressed by [Equation 5] has a minor diameter "b" with an upper limit of 50 mm or less, 10 mm or less, preferably 5 mm or less, 3 mm or less, and particularly preferably 2.8 mm or less. It is preferred that the minor diameter be smaller because the shock wave generating device can be downsized. However, when a convergent point outside the reflective part 12 is too close to the reflective part 12, a treatment effect becomes smaller, and hence a lower limit of the minor diameter "b" is 1.0 mm or more, preferably 1.5 mm or more, and particularly preferably 2.0 mm or more.

A ratio of major and minor diameters (a/b) of the ellipsoidal shape expressed by [Equation 5] is more than 1.2 and less than 2.0, preferably more than 1.3 and less than 1.6, and particularly preferably more than 1.4 and less than 1.6. When a/b is 2.0 or more, a convergence angle of the shock wave becomes shallower, and a high-pressure generation region has a shape that is elongated in the axial direction. In contrast, when a/b is 1.2 or less, the shock wave exhibits sharp convergence, but a focal length becomes disadvantageously shorter.

An upper limit of an outer diameter of the reflector 20 is 75 mm or less, preferably 10 mm or less, 5 mm or less, particularly preferably 3.5 mm or less, and 3 mm or less. In contrast, a lower limit of the outer diameter of the reflector 20 is 1.5 mm or more, preferably 2.5 mm or more, and particularly preferably 2.5 mm or more. When the outer diameter of the reflector 20 is more than 75 mm, it is difficult to pass the reflector 20 through the catheter. In contrast, when the outer diameter of the reflector 20 is less than 1.5 mm, it becomes difficult to generate a concave surface that is enough to reflect and converge the shock wave.

A material of the reflector 20 is not particularly limited, and examples thereof include acrylic and other synthetic resins, and brass, stainless steel, and other metals. When a metal is used, the concave surface 21 of the reflector 20 may be mirror-finished to increase a reflectance of the shock wave. Further, the metal and the liquid have a large difference in acoustic impedance, and hence can increase the reflectance of the shock wave as well. Meanwhile, when a synthetic resin is used, advantages, for example, excellent workability, are obtained. Through forming a metal film on the concave surface 21 of the reflector 20 by plating, for example, the reflectance of the shock wave can be increased.

It is required for the through hole 22 to be adjusted in size (inner diameter) as appropriate depending on an outer diameter of the optical fiber 11 to be used.

For the sealing body 23, a known thin film made of a synthetic resin having elasticity can be used. For example, a thin film made of polyethylene, polypropylene, polyethylene terephthalate, or other resin, or vinyl methyl silicone, methyl silicone, phenyl methyl silicone, or other silicone rubber can be used. A thickness of the thin film is selected as appropriate depending on its material, and in general, is preferably from 0.05 mm to 0.20 mm, and more preferably from 0.10 mm to 0.17 mm.

Further, the liquid 24 is a known liquid. Examples thereof include water and saline, and the liquid 24 is preferably pure water, and particularly preferably vacuum-degassed ultrapure water. The refractive index of the liquid 24 is lower than that of the core of the optical fiber, and is specifically from 1.0 to 1.5, and preferably from 1.3 to 1.4.

In order to perfuse a space formed between the concave surface 21 and the sealing body 23 with the liquid 24, a plumbing structure configured to communicate between water supply and water discharge pipes (not shown) and the space may be provided. As the plumbing structure, although not particularly limited, a plumbing structure including, as illustrated in FIG. 4A to FIG. 4G, a water supply pipe connecting portion 31 connected to the water supply pipe and a water discharge pipe connecting portion 32 connected to the water discharge pipe may be used. In FIG. 4A and FIG. 4B, a diameter of a front portion 22a of the through hole 22 is set larger than the diameter of the optical fiber 11 (to from about 2 to about 3 times the diameter of the optical fiber 11) on the concave surface 21 side, and the water supply pipe connecting portion 31 and the water discharge pipe connecting portion 32 are formed in a manner of branching off from the through hole 22. Further, in FIG. 4C to FIG. 4E, the diameter of the through hole 22 is similarly set larger than the diameter of the optical fiber 11 on the concave surface 21 side, and the water supply pipe connecting portion 31 and the water discharge pipe connecting portion 32 are formed in a manner of branching off from the through hole 22. In addition, a fixing member 33 configured to fix the optical fiber 11 is provided. Further, the through hole 22 is partitioned from the water supply pipe connecting portion 31 and the water discharge pipe connecting portion 32 by the fixing member 33. Still further, in FIG. 4F and FIG. 4G, the water supply pipe connecting portion 31 and the water discharge pipe connecting portion 32 are formed separately from the through hole 22.

As described above, in the shock wave generating device 10, the distal end of the laser beam convergence part 17 of the optical fiber 11 is fixed to the position at the distance Lx on the rear side from the focal point F inside the concave surface 21. Therefore, when the pulse laser beam is radiated from the distal end of the laser beam convergence part 17 to generate the shock wave in the liquid 24 inside the concave surface 21, the center point C of the shock wave and the focal point F can be made to substantially coincide with each other, and the shock wave reflected by the concave surface 21 can be efficiently converged to one point outside the reflective part 12.

2. Second Embodiment

Next, a shock wave generating device 10 according to a second embodiment of the present invention is described. In this embodiment, the concave surface 21 has a cut surface-of-revolution shape obtained by cutting a curved surface obtained by modifying the spheroid described above. The other components are the same as those in the first embodiment.

As described above, a wave front of the shock wave generated by the shock wave generating device 10 is distorted, for example, swells from a laser emission direction to the rear, to be aspherical. Therefore, when the concave surface 21 has a cut surface-of-revolution shape obtained by cutting the spheroid as in the first embodiment, differences occur in propagation distance over which the shock wave reflected at different portions of the concave surface 21 is converged to one point outside the reflective part 12, and it becomes difficult to efficiently reflect and converge the shock wave. In such a case, in order to equalize the propagation distances of the shock wave, it is preferred to use, for the concave surface 21, a cut surface-of-revolution shape obtained by cutting the curved surface obtained by modifying the spheroid.

The modification of the spheroid is not particularly limited as long as the generated shock wave can be efficiently reflected and converged to one point outside the reflective part 12. For example, the shock wave generating device may be actually produced, and the spheroid may be modified based on experimental data obtained therefrom, or may be modified based on results of simulation by a computer. It should be noted, however, that when it is considered to industrially manufacture the shock wave generating device, it is desired that the spheroid be modified based on the following [Equation 5] and [Equation 6].

That is, it is preferred to use, as the concave surface 21, a cut surface of revolution obtained by cutting the curved surface obtained by rotating a shape $(x_1, y_1)$ determined by [Equation 5] and [Equation 6] with the major axis of the ellipse expressed by [Equation 5] being the rotating axis, $$\frac{x^2}{a^2} + \frac{y^2}{b^2} = 1, 1.2 < \frac{a}{b} < 2.0, b \le 50 \quad \text{[Equation 5]}$$

$$x_1 = x + 0.5\Delta D |\cos \theta|, y_1 = y + 0.5\Delta D \sin \theta, 0 \le \theta \le \pi \quad \text{[Equation 6]}$$

provided that, in [Equation 6], "θ" represents, when a wave front of the shock wave at a certain time is represented by S, a wave front of ideal shock wave assuming shock wave to be completely spherical is represented by I, a center point of the ideal shock wave is represented by C, and a point on the wave front S and the wave front I that is located on an extension of a center axis of the optical fiber is represented by $S_f$, an angle around the center point C with respect to a line connecting the center point C and the point $S_f$, and "ΔD" represents, when points of intersection of a straight line in a radial direction of the ideal shock wave that passes through the center point C and has a central angle of θ, and the wave front S and the wave front I are represented by $S_\theta$ and $I_\theta$, respectively, a distance between the point of intersection $S_\theta$ and the point of intersection $I_\theta$.

Through the modification of the spheroid as described above, the propagation distances over which the shock wave generated at or near the focal point F of the spheroid before the modification is reflected at different portions of the concave surface 21 and is converged to one point outside the reflective part 12 can be equalized. As a result, even when the shock wave generated at the distal end of the optical fiber 11 is aspherical, the shock wave can be efficiently converged.

Figure 5:
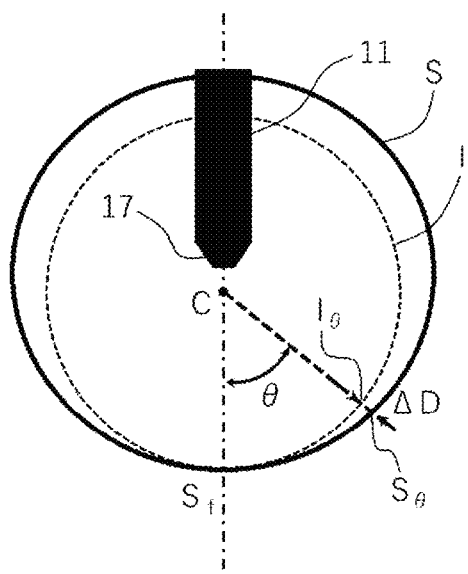
FIG. 5 is a schematic diagram for illustrating a wave front S of shock wave and a wave front I of ideal shock wave.
Figure 6:
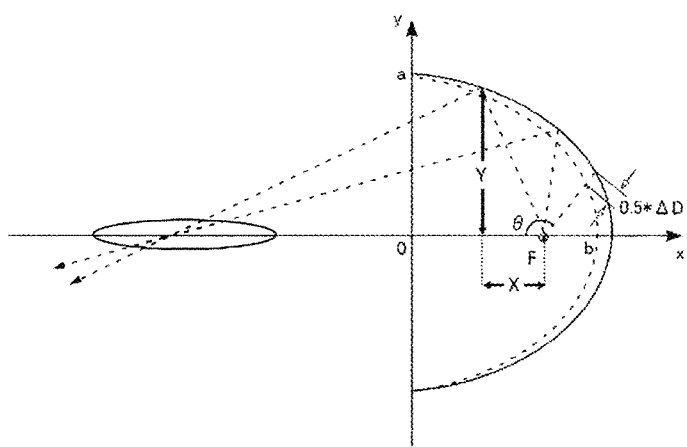
FIG. 6 is a schematic cross-sectional view in the axial direction for showing a propagation distance of the shock wave when the concave surface is a cut surface-of-revolution shape obtained by cutting a curved surface obtained by modifying a spheroid.

Next, a method of calculating a shape of the concave surface 21 of the shock wave generating device according to the second embodiment is described with reference to FIG. 5 and FIG. 6. The calculation method includes:

(1) a step (Step 1) of determining a wave front S of the shock wave generated by irradiating the liquid 24 with the pulse laser beam through the optical fiber 11;

(2) a step (Step 2) of determining a point of intersection $S_f$ at which the wave front S of the shock wave and an extended line of the center axis of the optical fiber 11 intersect each other on an opening side (front side) of the concave surface 21;

(3) a step (Step 3) of identifying the center point C of ideal shock wave;

(4) a step (Step 4) of determining a wave front I of the ideal shock wave having the center point C as its center and passing through the point of intersection $S_f$;

(5) a step (Step 5) of determining a relationship between a central angle θ with respect to a line connecting the center point C of the ideal shock wave and the point of intersection $S_f$, and a distance ΔD between a point $S_\theta$ on the wave front S of the shock wave and a point $I_\theta$ on the wave front of the ideal shock wave;

(6) a step (Step 6) of modifying, after the focal point F of the ellipsoidal shape and the center point C are made to coincide with each other, the ellipsoidal shape (x, y) expressed by the expression of [Expression 5] to the shape $(x_1, y_1)$ satisfying the expression of [Expression 6] based on the above-mentioned relationship; and (7) a step (Step 7) of cutting the curved surface obtained by rotating the modified shape with the major axis of the ellipse expressed by the expression of [Expression 5] being the rotating axis to obtain a cut surface of revolution.

$$\frac{x^2}{a^2} + \frac{y^2}{b^2} = 1, 1.2 < \frac{a}{b} < 2.0, b \le 50 \quad \text{[Expression 5]}$$

$$x_1 = x + 0.5\Delta D |\cos \theta|, y_1 = y + 0.5\Delta D \sin \theta, 0 \le \theta \le \pi \quad \text{[Expression 6]}$$

(1) Step 1

Step 1 is a step of determining the wave front S of the shock wave generated by irradiating the liquid 24 with the pulse laser beam through the optical fiber 11. A method of determining the wave front S is not particularly limited, and the wave front S can be determined by acquiring, with the use of a high-speed camera, for example, a high-speed image of the shock wave generated in the liquid by radiating the pulse laser beam from the optical fiber 11. The high-speed image may be a stereoscopic image, or a planar image depicted on a cross section taken along the rotating axis.

(2) Step 2

Step 2 is a step of determining the point of intersection $S_f$ on the opening side (front side) of the concave surface 21 at which the wave front S of the shock wave and the extended line of the center axis of the optical fiber 11 intersect each other. As illustrated in FIG. 5, a point on the front side (lower side in FIG. 5) at which the wave front S and the center axis of the optical fiber (laser beam convergence part 17) intersect each other is the point of intersection $S_f$.

(3) Step 3

Step 3 is a step of identifying the center point C of the shock wave (hereinafter referred to as "ideal shock wave") assumed to be completely spherical.

In this step, a cut spheroid is prepared as the concave surface 21, and after the center axis of the optical fiber 11 is adjusted to be coaxial with the rotating axis of the cut spheroid, the distal end of the optical fiber 11 (laser beam convergence part 17) is fixed to a suitable position on the rear side of the focal point F of the concave surface 21 (focal point located inside the reflective part 12 of focal points of the cut spheroid). At this time, it is preferred to arrange the distal end of the laser beam convergence part 17 so that the center point C of the shock wave that can be theoretically determined based on the shape of the laser beam convergence part 17, for example, coincides with the focal point F of the concave surface 21, that is, so that the relationship: Lx=d is satisfied. The shock wave is generated under this state, and the maximum overpressure $P_{max}$ of the shock wave reflected and converged to one point outside the reflective part 12 (focal point located outside the reflective part 12 of the focal points of the cut spheroid) is measured by a pressure sensor, for example. Thereafter, the laser beam convergence part 17 is moved in a rotating axis direction, and a position at which the maximum overpressure P. of the shock wave is maximized is determined. Then, the position at which the maximum overpressure P. of the shock wave is maximized is assumed to be a position at which the center point C of the shock wave and the focal point F of the concave surface 21 coincide with each other, and the position is identified as the center point C of the ideal shock wave.

When the center point C of the ideal shock wave is determined in this manner, Step 3 is independent of Step 1 and Step 2, and hence may be performed before, after, or simultaneously with Step 1 and Step 2.

The center point C of the ideal shock wave may be geometrically determined based on the high-speed image acquired in Step 1.

Figure 7:
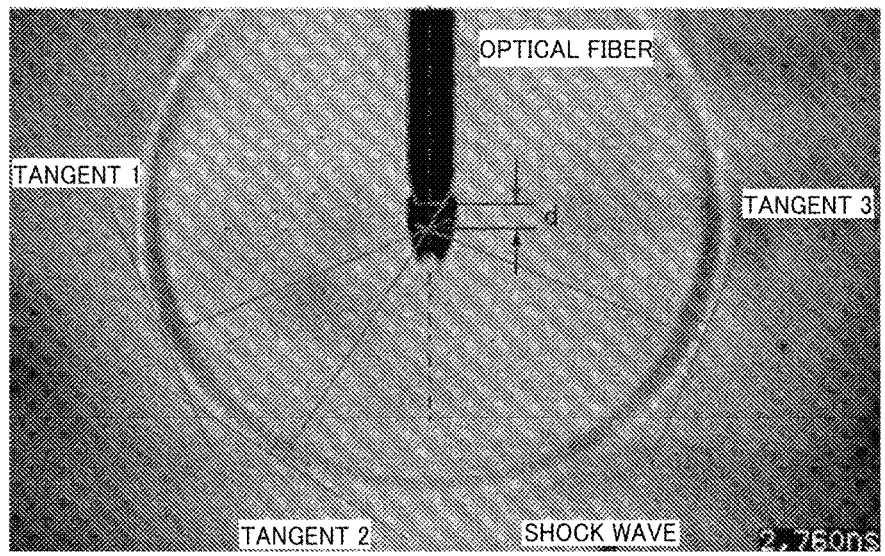
FIG. 7 is a high-speed image of the shock wave used to determine a center point of the ideal shock wave.

Specifically, as shown in FIG. 7, after a tangent at a suitable point on the wave front S of the shock wave is determined, the point of intersection of a line that passes through the point and is perpendicular to a tangential direction and the extended line of the center axis of the optical fiber 11 is determined, and the point of intersection is identified as the center point C of the wave front I of the ideal shock wave. In this method, it is preferred to perform a similar operation on a plurality of suitable points on the wave front S of the shock wave to identify center points C. In this case, it is preferred that points of intersection be identical, but when the points of intersection indicate a certain range, a point that is on the extension of the axis of the optical fiber and is closest to a center of the points is identified as the center point C of the ideal shock wave.

Further, a center of gravity of a shape defined by the wave front S of the shock wave may be determined based on the high-speed image acquired in Step 1, and the center of gravity may be identified as the center point C. In this case also, when the center of gravity deviates from the extended line of the center axis of the optical fiber 11, a point closest to the extended line is identified as the center point C of the ideal shock wave.

(4) Step 4

Returning to FIG. 5, Step 4 is a step of determining, after the center point C of the ideal shock wave and the point of intersection $S_f$ are determined, the wave front I of the ideal shock wave that passes through the point of intersection $S_f$. Specifically, the wave front I of the ideal shock wave can be determined by drawing a circle having a radius of a distance from the center point C to the point of intersection $S_f$ with the center point C being the center.

(5) Step 5

Step 5 is a step of determining the relationship between the central angle θ with respect to a straight line connecting the center point C of the ideal shock wave and the point of intersection $S_f$, and the distance ΔD between the point $S_θ$ on the wave front S of the shock wave and the point $I_θ$ on the wave front I of the ideal shock wave. Here, the point of intersection Se and a point of intersection $I_θ$ indicate points of intersection between a straight line in a radial direction of the ideal shock wave that passes through the center point C and has the central angle of θ, and the wave front S and the wave front I, respectively. It is preferred that those relationships be determined by generating a reference table or a reference graph. It is preferred that the angle θ be from 0° to 180°.

(6) Step 6

Step 6 is a step of modifying, after the focal point F of the ellipsoidal shape (focal point corresponding to the focal point located inside the reflective part 12 of the focal points of the cut spheroid described above) is superimposed on the center point C of the ideal shock wave, the ellipsoidal shape (x, y) expressed by the expression of [Equation 5] to the shape ($x_1$, $y_1$) satisfying the expression of [Equation 6] based on the relationship determined in Step 5. Through the formation of the concave surface 21 after modifying the ellipsoidal shape (x, y) expressed by the expression of [Equation 5] as described above, the propagation distances over which the generated aspherical shock wave is reflected at different portions of the concave surface 21 and is converted to one point outside the reflective part 12 can be equalized as illustrated in FIG. 6.

$$\frac{x^2}{a^2} + \frac{y^2}{b^2} = 1, 1.2 < \frac{a}{b} < 2.0, b \le 50 \quad \text{[Equation 5]}$$

$$x_1 = x + 0.5\Delta D |\cos \theta|, y_1 = y + 0.5\Delta D \sin \theta, 0 \le \theta \le \pi \quad \text{[Equation 6]}$$

Here, when the center of the ellipse expressed by the expression of [Equation 5] is defined as the origin (0, 0), the focal point F of the ellipse is expressed as:

$$(\sqrt{a^2-b^2}, 0)$$

As a result, the following expressions of [Equation 18] and [Equation 19] can be derived.

$$\cos \theta = \left(\frac{X}{\sqrt{X^2 + Y^2}}\right), X = \sqrt{a^2 - b^2} - x, Y = y \quad \text{[Equation 18]}$$

$$\sin \theta = \left(\frac{Y}{\sqrt{X^2 + Y^2}}\right), X = \sqrt{a^2 - b^2} - x, Y = y \quad \text{[Equation 19]}$$

The ellipsoidal shape of [Equation 5] is to be modified with the use of the above-mentioned sin θ and cos θ.

(7) Step 7

Step 7 is a step of cutting the curved surface obtained by rotating the shape obtained through the modification described above with the major axis of the ellipse expressed by the expression of [Equation 5] being the rotating axis to obtain a cut surface of revolution.

Through the formation of the concave surface 21 following the steps described above, the propagation distances over which the shock wave generated at or near the focal point F of the spheroid before the modification is reflected at different portions of the concave surface 21 and is converted to one point outside the reflective part 12 can be equalized. As a result, even when the shock wave generated at the distal end of the optical fiber 11 is aspherical, the shock wave can be efficiently converged, and the maximum overpressure $P_{max}$ of the shock wave can be increased dramatically.

EXAMPLES

Now, the present invention is described in more detail by means of Examples.

Examples 1-1 to 1-10 and Comparative Examples 1-1 to 1-4

First, the shock wave generating device 10 having the configuration described above was prepared, and an optimal position of the distal end of the optical fiber 11 (laser beam convergence part 17) was confirmed.

The reflective part 12 in the shock wave generating device 10 included: the reflector 20 having the concave surface 21, which was provided on the one end side, and had the cut surface-of-revolution shape obtained by cutting the spheroidal shape in which the major axis was the rotating axis, and the through hole 22, which was formed coaxially with the rotating axis, and into which the optical fiber 11 was to be inserted from the other end side; the sealing body 23 configured to seal the opening portion of the concave surface 21; and the liquid 24 charged between the concave surface 21 and the sealing body 23. The shape of the ellipse that served as the base of the concave surface 21, and dimensions, materials, and the like of respective members are provided below.

Shape of Ellipse that Served as the Base of Concave Surface 21

Shape of Ellipse
Minor Diameter (b): 3.50 mm
Major Diameter (a): 5.25 mm
Ellipticity (a/b): 1.50
Focal Length: 5.70 mm
Distance from Opening Portion to First Focal Point: 2.12 mm

Dimensions and Materials of Respective Members of Reflective Part 12

Reflector 20
Opening Diameter: 6.58 mm
Material: Brass
Sealing body 23
Material: Silicone Rubber
Thickness: 0.15 mm
Liquid 24
Ultrapure Water (Vacuum-degassed)
Refractive Index ($n_{liq}$): 1.301

Further, the configuration of the used optical fiber 11 is provided below. From those configurations and [Equation 2], the theoretical value "d" of the distance between the distal end of the laser beam convergence part 17 and the center point C of the shock wave is calculated to be 0.38 mm. A core surface of the laser beam convergence part 17 was formed by polishing with the use of abrasives having average particle sizes of 6 μm or less (Bare Fiber Polishing Film Package 5555.5 manufactured by ULTRA TEC) in order of decreasing average particle size.

Optical Fiber

Core
Material: Quartz (Dehydroxylated)
Core Diameter (M): 0.40 mm
Refractive Index ($n_{qtz}$): 1.437
Clad
Material: Quartz
Numerical Aperture (NA): 0.22

Laser Beam Convergence Part

Angle (α): 18.6°
Height (h): 0.21 mm

The shock wave generating device 10 satisfies, as shown in the following [Equation 20], Condition (I) assuming that all the pulse laser beam is totally reflected in the laser beam convergence part 17.

$$\frac{n_{qtz}}{n_{liq}} \sin\left(-0.5\alpha + \cos^{-1}\left(\frac{NA}{n_{qtz}}\right)\right) = 1.05 > 1 \quad \text{[Equation 20]}$$

Figure 8:
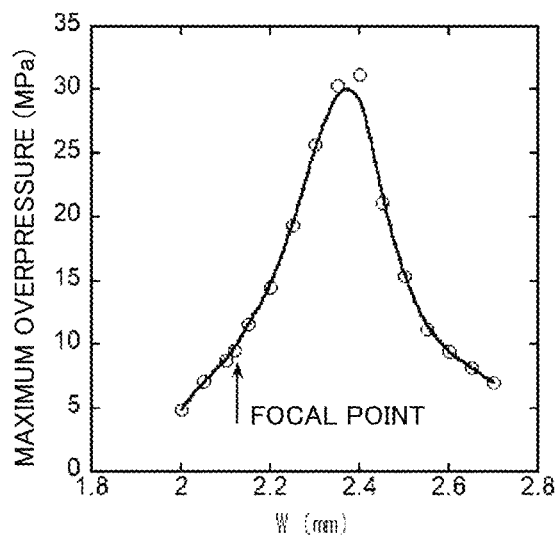
FIG. 8 is a graph for showing a relationship between a distal end position of the optical fiber and a maximum overpressure of the shock wave.

The shock wave generating device 10 was used to measure the maximum overpressure $P_{max}$ of the shock wave generated when a distal end position (distance: W from the opening portion of the concave surface 21 to the distal end of the laser beam convergence part 17) of the optical fiber 11 was changed with the use of a pressure sensor (Muller-Platte Needle Probe manufactured by Dr. Muller Instruments). Further, as the pulse laser beam, Ho:YAG laser was used. Results of the measurement are shown in Table 1 and FIG. 8. In those Examples and Comparative Examples, increasing amounts at respective positions were calculated with the maximum overpressure $P_{max}$ under a state in which the distal end position of the optical fiber 11 coincided with the focal point (W=2.12) being a reference value.

TABLE 1

| | Distance W (mm) from opening portion | Distance Lx* (mm) | Lx/d | Maximum Overpressure $P_{max}$ (MPa) | Increasing amount (times) |
|---|---|---|---|---|---|
| Comparative Example 1-1 | 2.00 | −0.12 | −0.43 | 4.89 | 0.51 |
| Comparative Example 1-2 | 2.05 | −0.07 | −0.25 | 7.12 | 0.75 |
| Comparative Example 1-3 | 2.10 | −0.02 | −0.07 | 8.75 | 0.92 |
| Comparative Example 1-4 | 2.12 | 0 | 0.00 | 9.55 | 1.00 (reference value) |
| Example 1-5 | 2.15 | 0.03 | 0.11 | 11.58 | 1.21 |
| Example 1-6 | 2.20 | 0.08 | 0.29 | 14.54 | 1.52 |
| Example 1-7 | 2.25 | 0.13 | 0.46 | 19.39 | 2.03 |
| Example 1-8 | 2.30 | 0.18 | 0.64 | 25.64 | 2.68 |
| Example 1-9 | 2.35 | 0.23 | 0.82 | 30.30 | 3.17 |
| Example 1-10 | 2.40 | 0.28 | 1.00 | 31.24 | 3.27 |
| Example 1-11 | 2.45 | 0.33 | 1.18 | 21.14 | 2.21 |
| Example 1-12 | 2.50 | 0.38 | 1.36 | 15.32 | 1.60 |

TABLE 1-continued

| Example | Distance W (mm) from opening portion | Distance Lx* (mm) | Lx/d | Maximum Overpressure $P_{max}$ (MPa) | Increasing amount (times) |
|---|---|---|---|---|---|
| Example 1-13 | 2.55 | 0.43 | 1.54 | 11.22 | 1.18 |
| Example 1-14 | 2.60 | 0.48 | 1.71 | 9.40 | 0.98 |

TABLE 1-continued

| Example | Distance W (mm) from opening portion | Distance Lx* (mm) | Lx/d | Maximum Overpressure $P_{max}$ (MPa) | Increasing amount (times) |
|---|---|---|---|---|---|
| Example 1-15 | 2.65 | 0.53 | 1.89 | 8.21 | 0.86 |
| Example 1-16 | 2.70 | 0.58 | 2.07 | 7.04 | 0.74 |

Note:
When the distal end of the optical fiber 11 (laser beam convergence part 17) was in front of the focal point F of the concave surface 21, the distance Lx had a negative sign.

From the above-mentioned results, it was confirmed that, when the distal end of the optical fiber 11 (laser beam convergence part 17) is on the rear side of the focal point F of the concave surface 21, the maximum overpressure $P_{max}$ of the shock wave reflected by the concave surface 21 was increased. It was also confirmed that, when Lx/d was 1.71, an increasing rate became 1 or less. That is, it was confirmed that, when 0<Lx/d≤1.5, the pulse laser beam was focused.

Examples 2-1 to 2-6

Next, the relationship between the distance Lx and the maximum overpressure $P_{max}$ when the shape of the distal end (laser beam convergence part 17) of the optical fiber 11 was changed was examined.

As the optical fiber 11, an optical fiber that was made of dehydroxylated quartz, and had a core diameter of the main body part of 400 μm, the refractive index $n_{qtz}$ of 1.437, the angle α of the laser beam convergence part 17 of from 0° to 60°, and the height "h" of the truncated cone of from 0.164 mm to 0.284 mm (optical fiber other than that having the angle α of 0°) was used.

Meanwhile, as the reflective part 12, a reflective part similar to that used in Examples 1-1 to 1-10 was used. In the shock wave generating device 10 according to those Examples, as the liquid, vacuum-degassed ultrapure water (refractive index $n_{liq}$: 1.301) was used.

Figure 9A:
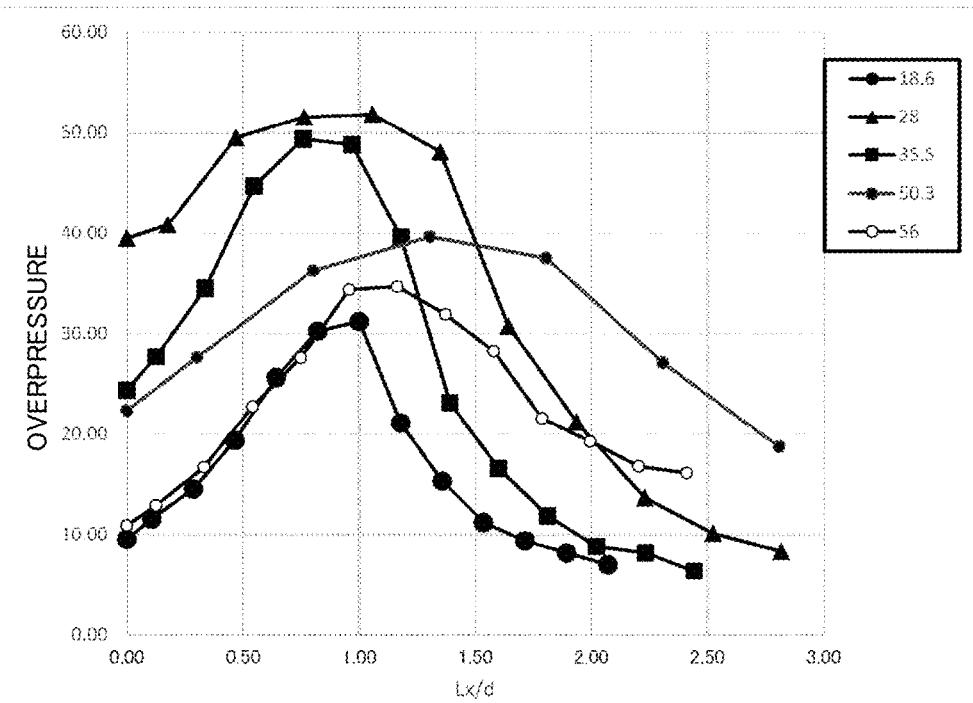
FIG. 9A is a graph for showing a relationship between Lx/d and a maximum overpressure $P_{max}$ of the shock wave when an angle α of a distal end of the optical fiber (laser beam convergence part) is from 0° to 60°.
Figure 9B:
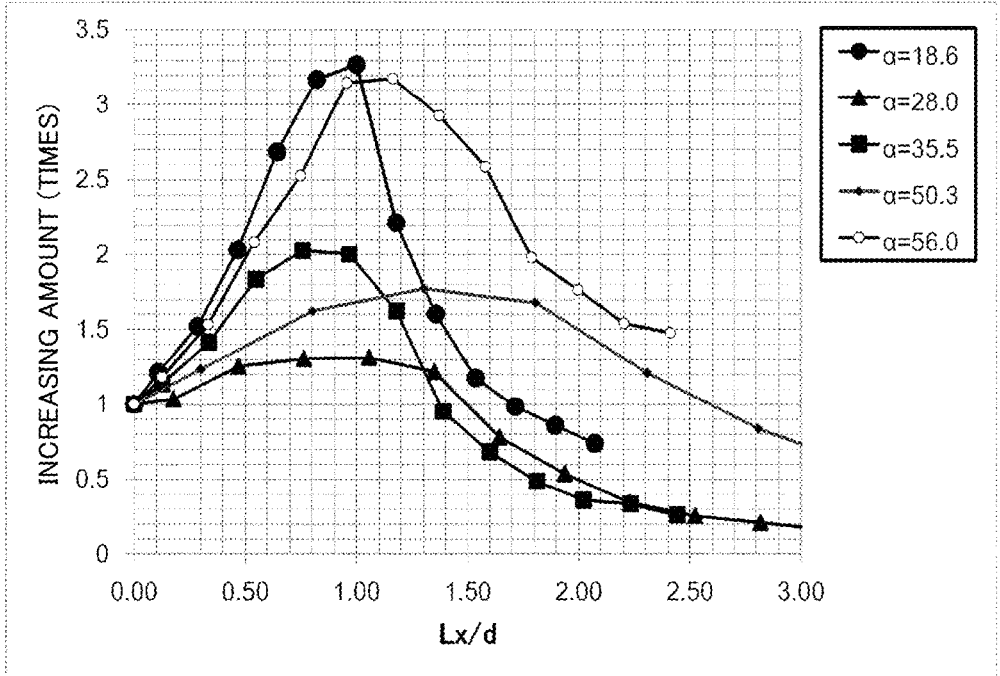
FIG. 9B is a graph for showing a relationship between Lx/d and an increasing rate of an overpressure.
Figure 10:
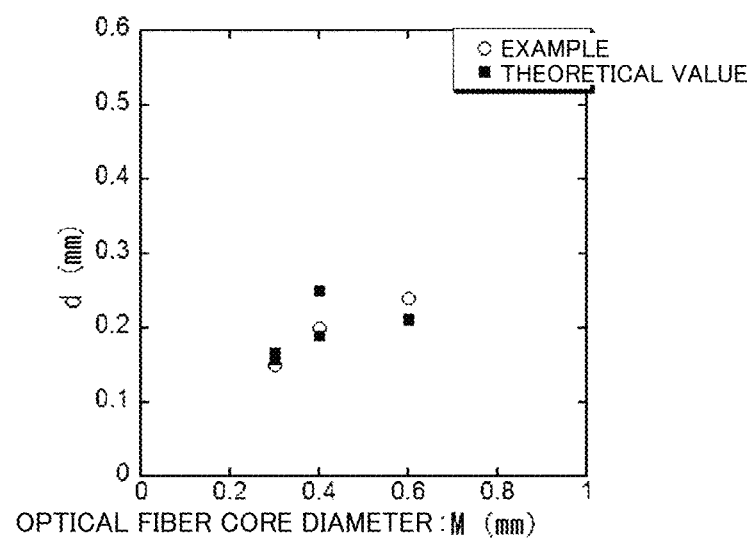
FIG. 10 is a graph for showing a relationship between a position of a center point C of the shock wave (position at the distance "d" from a distal end of the laser beam convergence part) and a core diameter M of the optical fiber when the angle α is 30°.

Through insertion of each optical fiber 11 into the through hole 22 of the reflector 20, the shock wave generating device 10 was formed. As in Examples 1-1 to 1-10, the maximum overpressure $P_{max}$ of the shock wave generated when the distal end position of the optical fiber 11 was changed was measured with the use of a pressure sensor, and the distance Lx at which the maximum overpressure P. of the shock wave was maximized was examined. Further, reflection states of the pulse laser beam in the laser beam convergence part 17 of the shock wave generating devices 10 were categorized into "I" when satisfying the above-mentioned Condition (I), "II" when satisfying the above-mentioned Condition (II), and "III" when satisfying the above-mentioned Condition (III). Results of the measurement are shown in Table 2, and FIG. 9A and FIG. 9B.

TABLE 2

| Example | Angle α (°) | Height "h" (mm) of truncated cone | Reflection state | Distance Lx (mm) | Lx/d | Maximum overpressure $P_{max}$ (Mpa) | Increasing amount (times) |
|---|---|---|---|---|---|---|---|
| 2-1 | 0 | — | — | 0.33 | — | 18.2 | — |
| 2-2 | 18.6 | 0.210 | I | 0.28 | 1.00 | 31.2 | 3.27 |
| 2-3 | 28.0 | 0.200 | I | 0.18 | 1.06 | 51.8 | 1.31 |
| 2-4 | 35.5 | 0.201 | II | 0.18 | 0.76 | 49.4 | 2.03 |
| 2-5 | 50.3 | 0.198 | II | 0.13 | 1.30 | 39.7 | 1.77 |
| 2-6 | 56.0 | 0.253 | III | 0.28 | 1.16 | 34.7 | 3.18 |

From the above-mentioned results, in Condition (I), when Lx/d was 1.00 and 1.06, the maximum overpressure $P_{max}$ was exhibited. Further, when 0<Lx/d≤1.5, the increasing amounts exceeded 1. In particular, when 0.5<Lx/d≤1.2, the maximum overpressure became higher than an overpressure of the reference value by 10 MPa or more.

In Condition (II), when Lx/d was 0.76 and 1.30, the maximum overpressure $P_{max}$ was exhibited. Further, when 0<Lx/d≤1.35, the increasing amounts exceeded 1. In particular, when 0.5≤Lx/d≤1.25, the maximum overpressure became higher than the overpressure of the reference value by 10 MPa or more. In Example 2-5 (α=50.3°), even when Lx/d exceeded 2, the increasing amount exceeded 1. It is considered that this is because, in Example 2-5 (α=50.3°) as compared to Example 2-4 (α=35.5°), internal reflection (total reflection) of the pulse laser beam in the laser beam convergence part 17 was abruptly reduced, and the effect of the pulse laser beam transmitted through the laser beam convergence part 17 became larger.

In Condition (III), when Lx/d was 1.16, the maximum overpressure $P_{max}$ was exhibited. Further, when 0<Lx/d (maximum measurement range: 2.41), the increasing amount exceeded 1. In particular, when 0.5≤Lx/d≤1.75, the maximum overpressure became higher than the overpressure of the reference value by 10 MPa or more.

In Example 2-3 (α=28°) and Example 2-4 (α=35.5°), the maximum values of the maximum overpressure were 51.8 MPa and 49.4 MPa, respectively, and was able be increased to around 50 MPa. Meanwhile, in Example 2-2, even with Condition (I), the maximum value of the maximum overpressure became smaller than that in Example 2-4 with Condition (II). It is considered that this is because, in Example 2-1, a propagation distance in the liquid to a focused position of the pulse laser beam is long, and the pulse laser beam is absorbed in the liquid before reaching the focused position.

Examples 3-1 to 3-3

As the optical fiber 11, optical fibers having the core diameter of the main body part 16 of 300 μm, 400 μm, and 600 μm, respectively, the angle α formed by the both sides of the isosceles trapezoid expressed by the cross section in the axial direction of the laser beam convergence part 17 of from 26.4° to 29.0°, and the height of the truncated cone of the laser beam convergence part 17 of from 0.17 mm to 0.44 mm were prepared.

Those optical fiber 11 was fixed to the reflector having the concave surface having an ellipticity of 1.5, which is obtained by cutting by a plane perpendicular to the major axis, to form the shock wave generating device 10. Those shock wave generating devices 10 also satisfy Condition (I) in which the laser beam convergence part 17 totally reflects all the pulse laser beam. As in Examples 1-1 to 1-10, the maximum overpressure $P_{max}$ of the shock wave generated when the distal end position of the optical fiber 11 was changed was measured with the use of a pressure sensor, and the distance Lx at which the maximum overpressure $P_{max}$ of the shock wave was maximized was examined. Results of the measurement are shown in Table 3, and FIG. 10 and FIG. 11A to FIG. 11C.

From those results, it was found that, when the angle α was near 30°, a relationship of [Equation 1] and [Equation 2] was established between a distance X from the distal end of the optical fiber to the center of the shock wave, and the core diameter M.

TABLE 3

| Example | Core diameter M (mm) | Angle α (°) | Height "h" (mm) of truncated cone | Reflection state | Theoretical value "d" (mm) | Distance Lx (mm) | Lx/d |
|---|---|---|---|---|---|---|---|
| 3-1 | 0.6 | 28.8 | 0.44 | I | 0.20 | 0.24 | 1.20 |
| 3-2 | 0.4 | 26.4 | 0.25 | I | 0.17 | 0.20 | 1.18 |
| 3-3 | 0.3 | 29.0 | 0.17 | I | 0.12 | 0.15 | 1.25 |

Example 4-1, Example 4-2, and Comparative Example 4-1

Finally, by means of Example 4-1, Example 4-2, and Comparative Example 4-1, a relationship between the shape of the concave surface 21 and the maximum overpressure $P_{max}$ was examined.

1. Design of Reflector

As the optical fiber 11, an optical fiber made of dehydroxylated quartz, which has the core diameter of the main body part of 400 μm, the refractive index $n_{qtz}$ of 1.437, the angle α of the laser beam convergence part 17 of 30°, and the height "h" of the truncated cone of 0.23 mm was prepared. This optical fiber 11 is inserted into a reflector 20 that is similar to that in Examples 1-1 to 1-10, and is adjusted so that the distance Lx is 0.23 mm to form the shock wave generating device 10. This shock wave generating device 10 also satisfies Condition (I) in which the laser beam convergence part 17 totally reflects all the pulse laser beam.

(1) Step 1

The shock wave generating device 10 was used to irradiate the liquid 24 with the pulse laser beam (wavelength: 2.1 μm, pulse width: 100 nsec, 43 mJ/pulse to 48 mJ/pulse, oscillation period: 1 Hz) to generate the shock wave, and photograph the wave front S with a high-speed camera (photography speed: 10 Mfps, exposure time: 50 nsec).

(2) Steps 2 to 4

From the thus-obtained high-speed image, the point of intersection $S_f$ of the wave front S of the shock wave and the extended line of the center axis of the optical fiber 11 was identified. From the results in Table 2, the position at 230 μm in front of the distal end of the laser beam convergence part 17 was assumed to be the center point C of the shock wave, and a circle (complete round) that had the center point C as the center, and passed through the point of intersection $S_f$ was defined as the wave front I of the ideal shock wave.

(3) Step 5

The angle (central angle) θ around the center point C with respect to the straight line connecting the point of intersection $S_f$ and the center point C, and the distance ΔD between the point $S_θ$ on the wave front S of the shock wave and the point $I_θ$ on the wave front I of the ideal shock wave were determined. Results of the determination are shown in FIG. 12.

(4) Step 6

Figure 12:
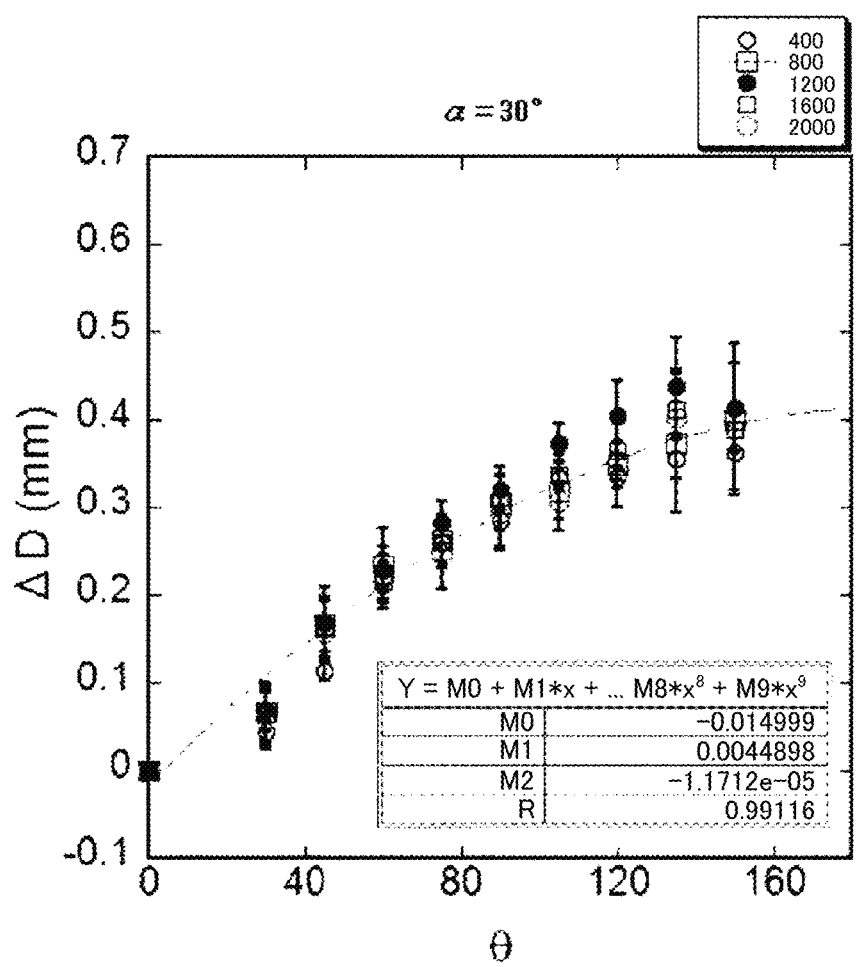
FIG. 12 is a graph for showing a relationship between an angle θ and a distance ΔD from a point of intersection $S_\theta$ to a point of intersection $I_\theta$ when the angle α of the distal end of the laser beam convergence part is 30°.

The ellipsoidal shape (x, y) expressed by the expression of [Equation 21] (case in which a/b=1.5 and b=1.8 in the expression of [Equation 5]) was modified, after the focal point F (of the focal points of the cut spheroid described above, the focal point corresponding to the focal point located inside the reflective part 12) of the ellipsoidal shape and the center point C of the ideal shock wave are superimposed with each other, to the shape $(x_1, y_1)$ satisfying the expression of [Equation 6] based on the relationship of FIG. 12 determined in Step 5.

$$\frac{x^2}{a^2} + \frac{y^2}{b^2} = 1, \frac{a}{b} = 1.5, b = 1.8 \qquad \text{[Equation 21]}$$

$$x_1 = x + 0.5\Delta D|\cos\theta|, y_1 = y + 0.5\Delta D \sin\theta, 0 \le \theta \le \pi \qquad \text{[Equation 6]}$$

(5) Step 7

The thus modified shape was rotated with a major axis of an ellipse expressed by the expression of [Equation 21] being a rotating axis to determine the shape of the concave surface 21 of the reflector 20. The reflector 20 was designed based on the shape of the concave surface 21.

2. Measurement of Maximum Overpressure $P_{max}$ of Shock Wave

As the optical fiber 11, an optical fiber made of dehydroxylated quartz, which had the core diameter of the main body part of 400 μm, the refractive index $n_{qtz}$ of 1.437, the angle α of the laser beam convergence part 17 of 30°, and the height "h" of the truncated cone of 0.23 mm, was prepared. The optical fiber 11 was attached to the reflector 20 in each of Examples 4-1 and 4-2 and Comparative Example 4-1 to form the shock wave generating device 10. Then, the shock wave was actually generated, and the maximum overpressure $P_{max}$ of the shock wave reflected and converged to one point outside the reflective part 12 was measured to examine the relationship between the shape of the concave surface 21 and the maximum overpressure $P_{max}$ of the shock wave.

Example 4-1

To the reflector 20 designed as described above, the optical fiber 11 was attached so that the distance Lx was adjusted to 0.23 mm to form the shock wave generating device 10.

The shock wave generating device 10 was used to generate the shock wave, and measure the maximum overpressure $P_{max}$ of the shock wave reflected and converged to one point outside the reflective part 12 with the use of a pressure sensor. At this time, the pulse laser beam radiated to generate the shock wave had the wavelength of 2.1 μm, the pulse width of 100 nsec, 43 mJ/pulse to 48 mJ/pulse, and the oscillation period of 1 Hz.

Example 4-2

Similarly to Example 4-1 except that a reflector having the concave surface 21 obtained by cutting the spheroidal shape having the ellipticity a/b of 1.5 by a plane perpendicular to the major axis was used as the reflector 20, the maximum overpressure $P_{max}$ of the shock wave was measured.

Comparative Example 4-1

Similarly to Example 4-1 except that a reflector having the concave surface 21 obtained by cutting the spheroidal shape having the ellipticity a/b of 1.5 by a plane perpendicular to the major axis was used as the reflector 20, and that the distance Lx was adjusted to be 0 mm (the distal end of the optical fiber 11 was adjusted to coincide with the focal point F of the concave surface 21), the maximum overpressure $P_{max}$ of the shock wave was measured. Results of the measurements are shown in Table 4 and FIG. 13.

TABLE 4

| | Shape of concave surface 21 | Distance Lx (mm) | Maximum overpressure $P_{max}$ (MPa) |
|---|---|---|---|
| Example 4-1 | Modified cut spheroid | 0.23 | 76.2 |
| Example 4-2 | Cut spheroid | 0.23 | 56.3 |
| Comparative Example 4-1 | Cut spheroid | 0 | 40.9 |

Figure 13:
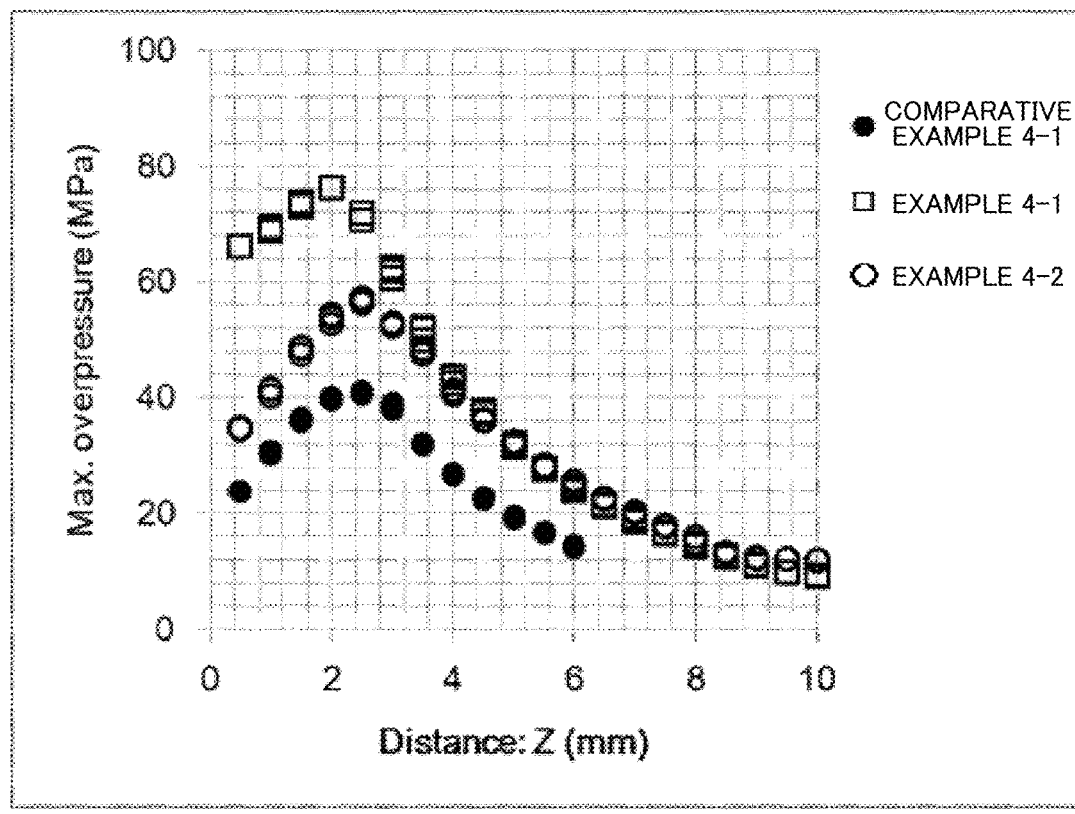
FIG. 13 is a graph for showing the maximum overpressure $P_{max}$ of the shock wave at a position separated by a distance Z in an emission direction of the pulse laser beam from the opening portion of the concave surface.

From Table 4 and FIG. 13, it was confirmed that, with the shock wave generating device according to Example 4-1 and Example 4-2, as compared to the shock wave generating device according to Comparative Example 4-1, the maximum overpressure $P_{max}$ of the reflected and converged shock wave was high. It was also confirmed that, with the shock wave generating device according to Example 4-1, the maximum overpressure $P_{max}$ of the shock wave was increased to about 1.35 times the maximum overpressure $P_{max}$ obtained with the shock wave generating device according to Example 4-2.

The invention claimed is:

1. A shock wave generating device, comprising:
   an optical fiber; and
   a reflective part, the shock wave generating device being configured to reflect and converge shock wave generated inside the reflective part to an outside of the reflective part, the reflective part including:
      a reflector having a concave surface and a through hole into which the optical fiber is to be inserted, the concave surface having a focal point;
      a sealing body configured to seal an opening portion of the concave surface; and
      a liquid to be charged between the concave surface and the sealing body,
   wherein the optical fiber includes a laser beam convergence part having a truncated cone shape,
   wherein a distance Lx from a distal end of the laser beam convergence part to the focal point satisfies [Equation 1] and [Equation 2]:

$$0 < \frac{L_x}{d} \le 1.5 \quad \text{[Equation 1]}$$

(I) When $\frac{n_{qtz}}{n_{liq}}\sin\left(-0.5\alpha + \cos^{-1}\left(\frac{NA}{n_{qtz}}\right)\right) > 1,$ [Equation 2]

$$d = \frac{0.5M - h \tan 0.5\alpha}{\tan\left(\sin^{-1}\frac{n_{qtz}}{n_{liq}}\sin\left(\alpha + \sin^{-1}\frac{NA}{n_{qtz}}\right)\right)}$$

(II) When $\frac{n_{qtz}}{n_{liq}}\sin\left(-0.5\alpha + \cos^{-1}\left(\frac{NA}{n_{qtz}}\right)\right) \le 1,$ $$\frac{n_{qtz}}{n_{liq}}\sin(0.5\pi - 0.5\alpha) > 1,$$

$$d = \frac{0.5M - h \tan 0.5\alpha}{\tan\left(\sin^{-1}\frac{n_{qtz}}{n_{liq}}\sin\left(\alpha - \sin^{-1}\frac{NA}{n_{qtz}}\right)\right)}$$

(provided that, in [Equation 2], "α" represents an angle formed by an isosceles trapezoid expressed by a cross section in an axial direction of the laser beam convergence part, "$n_{qtz}$" represents a refractive index of a core of the optical fiber, "$n_{liq}$" represents a refractive index of the liquid, "NA" represents a numerical aperture of the optical fiber, "M" represents a core diameter in a proximal end portion of the laser beam convergence part, and "h" represents a height of a truncated cone of the laser beam convergence part).

2. A shock wave ablation system, comprising:
   the shock wave generating device of claim 1; and
   a catheter having the shock wave generating device fixed to a distal end thereof.

3. A shock wave generating device, comprising:
   an optical fiber; and
   a reflective part, the shock wave generating device being configured to reflect and converge shock wave generated inside the reflective part to an outside of the reflective part, the reflective part including:
      a reflector having a concave surface and a through hole into which the optical fiber is to be inserted, the concave surface having a focal point;
      a sealing body configured to seal an opening portion of the concave surface; and
      a liquid to be charged between the concave surface and the sealing body,
   wherein the optical fiber includes a laser beam convergence part having a truncated cone shape,
   wherein a distance Lx from a distal end of the laser beam convergence part to the focal point satisfies [Equation 3] and [Equation 4]:

$$0 < \frac{L_x}{d} \le 2 \quad \text{[Equation 3]}$$

(III) When $\frac{n_{qtz}}{n_{liq}}\sin(0.5\pi - 0.5\alpha) \le 1,$ [Equation 4]

$$\frac{n_{qtz}}{n_{liq}}\sin\left(-0.5\alpha + 0.5\pi + \sin^{-1}\left(\frac{NA}{n_{qtz}}\right)\right) > 1,$$

$$d = (0.5M - h \tan(0.5\alpha)) \tan\left(\pi - 0.5\alpha - \sin^{-1}\left(\frac{n_{qtz}}{n_{liq}}\cos(0.5\alpha)\right)\right)$$

(provided that, in [Equation 4], "α" represents an angle formed by an isosceles trapezoid expressed by a cross section in an axial direction of the laser beam convergence part, "$n_{qtz}$" represents a refractive index of a core of the optical fiber, "$n_{liq}$" represents a refractive index of the liquid, "NA" represents a numerical aperture of the optical fiber, "M" represents a core diameter in a proximal end portion of the laser beam convergence part, and "h" represents a height of a truncated cone of the laser beam convergence part).

4. A shock wave ablation system, comprising:
   the shock wave generating device of claim 3; and
   a catheter having the shock wave generating device fixed to a distal end thereof.

5. A shock wave generating device, comprising:
   an optical fiber; and
   a reflective part,
the shock wave generating device being configured to reflect and converge shock wave generated inside the reflective part to an outside of the reflective part, the reflective part including:
   a reflector having a concave surface and a through hole into which the optical fiber is to be inserted;
   a sealing body configured to seal an opening portion of the concave surface; and
   a liquid to be charged between the concave surface and the sealing body,
wherein the optical fiber includes a laser beam convergence part,
wherein the concave surface is a cut surface of revolution obtained by cutting a curved surface obtained by rotating a shape ($x_1$, $y_1$) determined by [Equation 5] and [Equation 6] with a major axis of an ellipse expressed by [Equation 5] being a rotating axis, $$\frac{x^2}{a^2} + \frac{y^2}{b^2} = 1, \ 1.2 < \frac{a}{b} < 2.0, \ b \leq 50 \quad \text{[Equation 5]}$$

$$x_1 = x + 0.5\Delta D |\cos\theta|, \ y_1 = y + 0.5\Delta D \sin\theta, \ 0 \leq \theta \leq \pi \quad \text{[Equation 6]}$$

(provided that, in [Equation 6], "θ" represents, when a wave front of the shock wave at a certain time is represented by S, a wave front of ideal shock wave assuming shock wave to be completely spherical is represented by I, a center point of the ideal shock wave is represented by C, and a point on the wave front S and the wave front I that is located on an extension of a center axis of the optical fiber is represented by $S_f$, an angle around the center point C with respect to a line connecting the center point C and the point $S_f$, and "ΔD" represents, when points of intersection of a straight line in a radial direction of the ideal shock wave that passes through the center point C and has a central angle of θ, and the wave front S and the wave front I are represented by $S_\theta$ and $I_\theta$, respectively, a distance between the point of intersection $S_\theta$ and the point of intersection $I_\theta$).

6. A shock wave ablation system, comprising:
   the shock wave generating device of claim 5; and
   a catheter having the shock wave generating device fixed to a distal end thereof.

\* \* \* \* \*